(12) United States Patent
Kautz et al.

(10) Patent No.: US 7,718,668 B2
(45) Date of Patent: *May 18, 2010

(54) SALTS OF 6-HETEROCYCLE SUBSTITUTED HEXAHYDROPHENANTHRIDINE DERIVATIVES

(75) Inventors: Ulrich Kautz, Allensbach (DE); Matthias Webel, Radolfzell (DE); Christian Scheufler, Engen-Neuhausen (DE); Rolf-Peter Hummel, Radolfzell (DE)

(73) Assignee: Nycomed GmbH, Constance (DE)

( * ) Notice: Subject to any disclaimer, the term of this patent is extended or adjusted under 35 U.S.C. 154(b) by 85 days.

This patent is subject to a terminal disclaimer.

(21) Appl. No.: 11/884,934

(22) PCT Filed: Mar. 1, 2006

(86) PCT No.: PCT/EP2006/060377

§ 371 (c)(1),
(2), (4) Date: Aug. 23, 2007

(87) PCT Pub. No.: WO2006/092422

PCT Pub. Date: Sep. 8, 2006

(65) Prior Publication Data

US 2008/0194587 A1    Aug. 14, 2008

(30) Foreign Application Priority Data

Mar. 2, 2005  (EP) ................. 05101619
Sep. 14, 2005 (EP) ................. 05108442

(51) Int. Cl.
*C07D 401/04* (2006.01)
*C07D 403/04* (2006.01)
*A61K 31/473* (2006.01)
*A61K 31/501* (2006.01)
*A61K 31/506* (2006.01)

(52) U.S. Cl. ............ 514/298; 514/252.01; 514/252.1; 546/108; 544/238; 544/298; 544/310; 544/336

(58) Field of Classification Search ............. 546/108; 544/238, 298, 310, 336; 514/298, 252.01, 514/252.1, 256, 269
See application file for complete search history.

(56) References Cited

U.S. PATENT DOCUMENTS

| 6,008,215 | A  | 12/1999 | Flockerzi |
| 6,121,279 | A  | 9/2000  | Gutterer |
| 6,127,378 | A  | 10/2000 | Gutterer |
| 6,191,138 | B1 | 2/2001  | Gutterer |
| 6,214,839 | B1 | 4/2001  | Gutterer |
| 6,306,869 | B1 | 10/2001 | Flockerzi |
| 6,410,551 | B1 | 6/2002  | Gutterer |
| 6,476,025 | B1 | 11/2002 | Gutterer |
| 6,479,505 | B1 | 11/2002 | Gutterer |
| 6,534,518 | B1 | 3/2003  | Gutterer |
| 6,534,519 | B1 | 3/2003  | Gutterer |
| 6,538,005 | B2 | 3/2003  | Gutterer |
| 6,884,802 | B2 | 4/2005  | Schmidt |
| 6,936,622 | B2 | 8/2005  | Flockerzi |
| 7,329,676 | B2 | 2/2008  | Kautz et al. |
| 7,423,046 | B2 | 9/2008  | Kautz |
| 7,585,872 | B2 | 9/2009  | Kautz et al. |
| 7,632,844 | B2 | 12/2009 | Kautz et al. |
| 2004/0038979 | A1 | 2/2004 | Schmidt |
| 2004/0097537 | A1 | 5/2004 | Kautz et al. |
| 2005/0239817 | A1 | 10/2005 | Kautz et al. |
| 2005/0239818 | A1 | 10/2005 | Kautz et al. |
| 2006/0116518 | A1 | 6/2006 | Krautz et al. |
| 2007/0167482 | A1 | 7/2007 | Kautz |
| 2007/0185149 | A1 | 8/2007 | Kautz et al. |
| 2007/0191413 | A1 | 8/2007 | Kautz et al. |
| 2007/0191414 | A1 | 8/2007 | Kautz et al. |
| 2007/0259909 | A1 | 11/2007 | Kautz et al. |
| 2008/0319067 | A1 | 12/2008 | Kautz et al. |
| 2009/0170892 | A1 | 7/2009 | Kautz et al. |

FOREIGN PATENT DOCUMENTS

| EP | 0 490 823 A1 | 12/1991 |
| EP | 1270577 | 12/2006 |
| WO | 97/28131 A1 | 8/1997 |
| WO | 97/35854 A1 | 10/1997 |
| WO | WO 98/21208 | 5/1998 |
| WO | WO 98/40382 | 9/1998 |
| WO | WO 98/55481 | 12/1998 |
| WO | 99/05111 A1 | 2/1999 |
| WO | 99/05112 A1 | 2/1999 |
| WO | 99/05113 A1 | 2/1999 |
| WO | 99/57118 A1 | 11/1999 |

(Continued)

OTHER PUBLICATIONS

Cecil Textbook of Medicine, edited by Bennet, J.C., and Plum F., 20th edition, vol. 1, 1004-1010, 1996.*

(Continued)

*Primary Examiner*—Venkataraman Balasubramanian
(74) *Attorney, Agent, or Firm*—The Nath Law Group; Sheldon M. McGee; Robert M. Joynes

(57) ABSTRACT

The invention relates to salts of 6-heteroaryl substituted hexahydrophenanthridine PDE4-inhibiting compounds, which can be used in the pharmaceutical industry for the production of pharmaceutical compositions for use, e.g., in treatment of airway disorders.

5 Claims, No Drawings

FOREIGN PATENT DOCUMENTS

| | | |
|---|---|---|
| WO | WO 00/12501 | 3/2000 |
| WO | 00/42017 A1 | 7/2000 |
| WO | 00/42018 A1 | 7/2000 |
| WO | 00/42019 A1 | 7/2000 |
| WO | 00/42020 A1 | 7/2000 |
| WO | 00/42034 A1 | 7/2000 |
| WO | WO 01/51470 | 7/2001 |
| WO | 02/05616 A1 | 1/2002 |
| WO | 02/06238 A1 | 1/2002 |
| WO | 02/06270 A1 | 1/2002 |
| WO | 02/066476 A1 | 8/2002 |
| WO | 2004/018431 A2 | 3/2004 |
| WO | 2004/018431 A3 | 3/2004 |
| WO | 2004/019944 A1 | 3/2004 |
| WO | 2004/019945 A1 | 3/2004 |
| WO | WO 04/018465 | 3/2004 |
| WO | 2005/077906 A1 | 8/2005 |
| WO | 2005/084104 A2 | 9/2005 |
| WO | 2005/085203 A1 | 9/2005 |
| WO | 2005/085225 A1 | 9/2005 |
| WO | 2005/087744 A1 | 9/2005 |
| WO | 2005/087745 A1 | 9/2005 |
| WO | 2005/090311 A1 | 9/2005 |
| WO | WO-2005/085225 A1 * | 9/2005 |
| WO | 2006/092422 A1 | 9/2006 |

OTHER PUBLICATIONS

West, Anthony R., Solid State Chemistry and its Applications, Wiley, New York, 1988, pp. 358 & 365.*

Vippagunta et al., Advanced Drug Delivery Reviews 48: 3-26, 2001.*

Kroegel et al., Expert Opin. Investig. Drugs, 16(1), 109-124, 2007.*

Schmidt et al., "The phosphodiesterase 4 inhibitor roflumilast is effective in the treatment of allergic rehinitis." J. Allergy Clin. Immunol., v.108:4, 530-536 (2001).

Montana and Dyke, "Chapter 5. Phosphodiesterase 4 Inhibitors." J. Annual Reports Med. Chem., v.36, pp. 41-56 (2001).

Dyke and Montana, "Update on the therapeutic potential of PDE4 inhibitors." Expert Opin. Investig. Drugs, v.11:1, pp. 1-13 (2002).

Souness et al., "Immunosuppressive and anti-inflammatory effects of cyclic AMP phosphodiesterase (PDE) type 4 inhibitors." Immunopharmacology, v.47, pp. 127-162 (2000).

Baumer et al., "Highly Selective Phosphodiesterase 4 Inhibitors for the Treatment of Allergic Skin Diseases and Psoriasis", Infl. and Allergy—Drug Targets, 2006, 6, 17-26.

Dorwald, F. A., Side Reactions in Organic Synthesis, 2005 p. IX of Preface.

Patel et al., "Treatment of non-insulin-dependent diabetes mellitus", Expert Opin. Investig. Drugs, 2003, 12(4):623-633.

Kamentani et al., "Cyclised Products in the Synthesis of 6-Substituted Phananthridines by Phenolic Cyclisation", J. Chem. Soc., pp. 1805-08, 1971.

Govindachari et al., "Application of the Bruckner Method to the Synthesis of Phenanthridine Derivatives", J. Chem. Soc., pp. 4280-83, 1956.

Sugasawa et al., "Syhthese Partiell Hydrierter Phenanthridin-Derivate (I)", Chem. Ber., pp. 675-678, 1939.

* cited by examiner

SALTS OF 6-HETEROCYCLE SUBSTITUTED HEXAHYDROPHENANTHRIDINE DERIVATIVES This application was filed under 35 U.S.C. 371 as a national stage of PCT/EP2006/060377, filed Mar. 1, 2006.

FIELD OF APPLICATION OF THE INVENTION

The invention relates to salts of active compounds, which can be used in the pharmaceutical industry for the production of pharmaceutical compositions.

KNOWN TECHNICAL BACKGROUND

The International Patent applications WO99/57118 and WO02/05616 describe 6-phenylphenanthridines as PDE4 inhibitors.

In the International Patent application WO99/05112 substituted 6-alkylphenanthridines are described as bronchial therapeutics.

In the European Patent application EP 0490823 dihydroisoquinoline derivatives are described which are said to be useful in the treatment of asthma.

The International Patent application WO00/42019 discloses 6-arylphenanthridines as PDE4 inhibitors.

The International Patent application WO02/06270 disdoses 6-heteroarylphenanthridines as PDE4 inhibitors.

The International Patent application WO97/35854 discloses phenanthridines substituted in the 6-position as PDE4 inhibitors.

The International Patent applications WO2004/019944 and WO2004/019945 disclose hydroxy-substituted 6-phenylphenanthridines as PDE4 inhibitors.

The International Patent application WO2005/085225 discloses hydroxyl-6 heteroarylphenanthridine derivatives as active compounds, the disclosure of which is incorporated herein.

DESCRIPTION OF THE INVENTION

It has now been found that the novel compounds (i.e. salts of active free bases) described in greater detail below have surprising and particularly advantageous properties.

Thus, the invention relates, in a first aspect, to the following salts (2R,4aR,10bR)-6-(2,6-Dimethoxy-pyridin-3-yl)-9-ethoxy-8-methoxy-1,2,3,4,4a, 10b-hexahydro-phenanthridin-2-ol hydrochloride;

(2R,4aR,10bR)-9-Ethoxy-8-methoxy-6-pyrimidin-5-yl-1,2,3,4,4a, 10b-hexahydro-phenanthridin-2-ol hydrochloride;

(2R,4aR,10bR)-9-Ethoxy-8-methoxy-6-(6-pyrazol-1-yl-pyridin-3-yl)-1,2,3,4,4a, 10b-hexahydro-phenanthridin-2-ol hydrochloride;

(2R,4aR,10bR)-9-Ethoxy-8-methoxy-6-(2-methoxy-pyrimidin-5-yl)-1,2,3,4,4a, 10b-hexahydro-phenanthridin-2-ol hydrochloride;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol hydrochloride;

(2R,4aR,10bR)-9-Ethoxy-8-methoxy-6-pyrazin-2-yl-1,2,3,4,4a, 10b-hexahydro-phenanthridin-2-ol hydrochloride;

(2R,4aR,10bR)-6-(3,6-Dimethoxy-pyridazin-4-yl)-9-ethoxy-8-methoxy-1,2,3,4,4a, 10b-hexahydro-phenanthridin-2-ol hydrochloride;

(2R,4aR,10bR)-9-Ethoxy-8-methoxy-6-(6-methoxy-pyridin-3-yl)-1,2,3,4,4a, 10b-hexahydro-phenanthridin-2-ol hydrochloride;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol hydrochloride;

(2R,4aR,10bR)-6-(4,6-Dimethoxy-pyrdin-3-yl)-9-ethoxy-8-methoxy-1,2,3,4,4a, 10b-hexahydro-phenanthridin-2-ol hydrochloride;

(2R,4aR,10bR)-6-(2-Dimethylamino-pyrimidin-5-yl)-9-ethoxy-8-methoxy-1,2,3,4,4a, 10b-hexahydro-phenanthridin-2-ol hydrochloride;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one hydrochloride;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one hydrochloride;

(2R,4aR,10bR)-6-(2,6-Dimethoxy-pyridin-3-yl)-9-ethoxy-8-methoxy-1,2,3,4,4a, 10b-hexahydro-phenanthridin-2-ol sulfate;

(2R,4aR,10bR)-9-Ethoxy-8-methoxy-6-(2-methoxy-pyrimidin-5-yl)-1,2,3,4,4a, 10b-hexahydro-phenanthridin-2-ol sulfate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol sulfate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol sulfate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol sulfate;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol sulfate;

(2R,4aR,10bR)-6-(4,6-Dimethoxy-pyridin-3-yl)-9-ethoxy-8-methoxy-1,2,3,4,4a, 10b-hexahydro-phenanthridin-2-ol sulfate;

(2R,4aR,10bR)-6-(2-Dimethylamino-pyrimidin-5-yl)-9-ethoxy-8-methoxy-1,2,3,4,4a, 10b-hexahydro-phenanthridin-2-ol sulfate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one sulfate;

(2R,4aR,10bR)-6-(2,6-Dimethoxy-pyridin-3-yl)-9-ethoxy-8-methoxy-1,2,3,4,4a, 10b-hexahydro-phenanthridin-2-ol methansulfonate;

(2R,4aR,10bR)-9-Ethoxy-8-methoxy-6-pyrimidin-5-yl-1,2,3,4,4a, 10b-hexahydro-phenanthridin-2-ol methansulfonate;

(2R,4aR,10bR)-9-Ethoxy-8-methoxy-6-(2-methoxy-pyrimidin-5-yl)-1,2,3,4,4a, 10b-hexahydro-phenanthridin-2-ol methansulfonate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol methansulfonate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol methansulfonate;

(2R,4aR,10bR)-9-Ethoxy-8-methoxy-6-pyrazin-2-yl-1,2,3, 4,4a, 10b-hexahydro-phenanthridin-2-ol methansulfonate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol methansulfonate;

(2R,4aR,10bR)-9-Ethoxy-8-methoxy-6-(6-methoxy-pyridin-3-yl)-1,2,3,4,4a, 10b-hexahydro-phenanthridin-2-ol methansulfonate;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol methansulfonate;

(2R,4aR,10bR)-6-(4,6-Dimethoxy-pyridin-3-yl)-9-ethoxy-8-methoxy-1,2,3,4,4a, 10b-hexahydro-phenanthridin-2-ol methansulfonate;

(2R,4aR,10bR)-6-(2-Dimethylamino-pyrimidin-5-yl)-9-ethoxy-8-methoxy-1,2,3,4,4a, 10b-hexahydro-phenanthridin-2-ol methansulfonate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one methansulfonate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one methansulfonate;

(2R,4aR,10bR)-6-(2,6-Dimethoxy-pyridin-3-yl)-9-ethoxy-8-methoxy-1,2,3,4,4a, 10b-hexahydro-phenanthridin-2-ol citrate;

(2R,4aR,10bR)-9-Ethoxy-8-methoxy-6-(6-pyrazol-1-yl-pyridin-3-yl)-1,2,3,4,4a, 10b-hexahydro-phenanthridin-2-ol citrate;

(2R,4aR,10bR)-9-Ethoxy-8-methoxy-6-(2-methoxy-pyrimidin-5-yl)-1,2,3,4,4a, 10b-hexahydro-phenanthridin-2-ol citrate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol citrate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol citrate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol citrate;

(2R,4aR,10bR)-9-Ethoxy-8-methoxy-6-(6-methoxy-pyridin-3-yl)-1,2,3,4,4a, 10b-hexahydro-phenanthridin-2-ol citrate;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol citrate;

(2R,4aR,10bR)-6-(4,6-Dimethoxy-pyridin-3-yl)-9-ethoxy-8-methoxy-1,2,3,4,4a, 10b-hexahydro-phenanthridin-2-ol citrate;

(2R,4aR,10bR)-6-(2-Dimethylamino-pyrimidin-5-yl)-9-ethoxy-8-methoxy-1,2,3,4,4a, 10b-hexahydro-phenanthridin-2-ol citrate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one citrate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one citrate;

(2R,4aR,10bR)-6-(2,6-Dimethoxy-pyridin-3-yl)-9-ethoxy-8-methoxy-1,2,3,4,4a, 10b-hexahydro-phenanthridin-2-ol L-tartrate;

(2R,4aR,10bR)-9-Ethoxy-8-methoxy-6-pyrimidin-5-yl-1,2,3,4,4a, 10b-hexahydro-phenanthridin-2-ol L-tartrate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol L-tartrate;

(2R,4aR,10bR)-9-Ethoxy-8-methoxy-6-(2-methoxy-pyrimidin-5-yl)-1,2,3,4,4a, 10b-hexahydro-phenanthridin-2-ol L-tartrate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol L-tartrate;

(2R,4aR,10bR)-9-Ethoxy-8-methoxy-6-pyrazin-2-yl-1,2,3,4,4a, 10b-hexahydro-phenanthridin-2-ol L-tartrate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol L-tartrate;

(2R,4aR,10bR)-9-Ethoxy-8-methoxy-6-(6-methoxy-pyridin-3-yl)-1,2,3,4,4a, 10b-hexahydro-phenanthridin-2-ol L-tartrate;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol L-tartrate;

(2R,4aR,10bR)-6-(4,6-Dimethoxy-pyridin-3-yl)-9-ethoxy-8-methoxy-1,2,3,4,4a, 10b-hexahydro-phenanthridin-2-ol L-tartrate;

(2R,4aR,10bR)-6-(2-Dimethylamino-pyrimidin-5-yl)-9-ethoxy-8-methoxy-1,2,3,4,4a, 10b-hexahydro-phenanthridin-2-ol L-tartrate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one L-tartrate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one L-tartrate;

(2R,4aR,10bR)-6-(2,6-Dimethoxy-pyridin-3-yl)-9-ethoxy-8-methoxy-1,2,3,4,4a, 10b-hexahydro-phenanthridin-2-ol D-tartrate;

(2R,4aR,10bR)-9-Ethoxy-8-methoxy-6-(2-methoxy-pyrimidin-5-yl)-1,2,3,4,4a, 10b-hexahydro-phenanthridin-2-ol D-tartrate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol D-tartrate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol D-tartrate;

(2R,4aR,10bR)-9-Ethoxy-8-methoxy-6-pyrazin-2-yl-1,2,3,4,4a, 10b-hexahydro-phenanthridin-2-ol D-tartrate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol D-tartrate;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol D-tartrate;

(2R,4aR,10bR)-6-(4,6-Dimethoxy-pyridin-3-yl)-9-ethoxy-8-methoxy-1,2,3,4,4a, 10b-hexahydro-phenanthridin-2-ol D-tartrate;

(2R,4aR,10bR)-6-(2-Dimethylamino-pyrimidin-5-yl-9-ethoxy-8-methoxy-1,2,3,4,4a,10b-hexahydro-phenanthridin-2-ol D-tartrate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one D-tartrate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one D-tartrate;

(2R,4aR,10bR)-6-(2,6-Dimethoxy-pyridin-3-yl)-9-ethoxy-8-methoxy-1,2,3,4,4a, 10b-hexahydro-phenanthridin-2-ol meso-tartrate;

(2R,4aR,10bR)-9-Ethoxy-8-methoxy-6-pyrimidin-5-yl-1,2,3,4,4a, 10b-hexahydro-phenanthridin-2-ol meso-tartrate;

(2R,4aR,10bR)-9-Ethoxy-8-methoxy-6-(2-methoxy-pyrimidin-5-yl)-1,2,3,4,4a, 10b-hexahydro-phenanthridin-2-ol meso-tartrate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol meso-tartrate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol meso-tartrate;

(2R,4aR,10bR)-9-Ethoxy-8-methoxy-6-pyrazin-2-yl-1,2,3,4,4a, 10b-hexahydro-phenanthridin-2-ol meso-tartrate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol meso-tartrate;

(2R,4aR,10bR)-6-(2-Dimethylamino-4-methoxy-pyrmidin-5-yl)-9-ethoxy-8-methoxy-1,2,3,4,4a, 10b-hexahydro-phenanthridin-2-ol meso-tartrate;

(2R,4aR,10bR)-6-(4,6-Dimethoxy-pyridin-3-yl)-9-ethoxy-8-methoxy-1,2,3,4,4a, 10b-hexahydro-phenanthridin-2-ol meso-tartrate;

(2R,4aR,10bR)-6-(2-Dimethylamino-pyrimidin-5-yl)-9-ethoxy-8-methoxy-1,2,3,4,4a, 10b-hexahydro-phenanthridin-2-ol meso-tartrate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one meso-tartrate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one meso-tartrate;

(2R,4aR,10bR)-6-(2,6-Dimethoxy-pyridin-3-yl)-9-ethoxy-8-methoxy-1,2,3,4,4a, 10b-hexahydro-phenanthridin-2-ol D-malate;

(2R,4aR,10bR)-9-Ethoxy-8-methoxy-6-(6-pyrazol-1-yl-pyridin-3-yl)-1,2,3,4,4a, 10b-hexahydro-phenanthridin-2-ol D-malate;

(2R,4aR,10bR)-9-Ethoxy-8-methoxy-6-(2-methoxy-pyrimidin-5-yl)-1,2,3,4,4a, 10b-hexahydro-phenanthridin-2-ol D-malate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol D-malate;

(2R,4aR,10bR)-6-(3,6-Dimethoxy-pyridazin-4-y)-9-ethoxy-8-methoxy-1,2,3,4,4a, 10b-hexahydro-phenanthridin-2-ol D-malate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-malate;

(2R,4aR,10bR)-6-(4,6-Dimethoxy-pyridin-3-yl)-9-ethoxy-8-methoxy-1,2,3,4,4a, 10b-hexahydro-phenanthridin-2-ol D-malate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one D-malate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one D-malate;

(2R,4aR,10bR)-6-(2,6-Dimethoxy-pyridin-3-yl)-9-ethoxy-8-methoxy-1,2,3,4,4a, 10b-hexahydro-phenanthridin-2-ol L-malate;

(2R,4aR,10bR)-9-Ethoxy-8-methoxy-6-pyrimidin-5-yl-1,2,3,4,4a, 10b-hexahydro-phenanthridin-2-ol L-malate;

(2R,4aR,10bR)-9-Ethoxy-8-methoxy-6-(2-methoxy-pyrimidin-5-yl)-1,2,3,4,4a, 10b-hexahydro-phenanthridin-2-ol L-malate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol L-malate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol L-malate;

(2R,4aR,10bR)-6-(3,6-Dimethoxy-pyridazin-4-y)-9-ethoxy-8-methoxy-1,2,3,4,4a, 10b-hexahydro-phenanthridin-2-ol L-malate;

(2R,4aR,10bR)-6-(2-Dimethylamino-4-methoxy-pyrmidin-5-yl)-9-ethoxy-8-methoxy-1,2,3,4,4a, 10b-hexahydro-phenanthridin-2-ol L-malate;

(2R,4aR,10bR)-6-(4,6-Dimethoxy-pyridin-3-yl)-9-ethoxy-8-methoxy-1,2,3,4,4a, 10b-hexahydro-phenanthridin-2-ol L-malate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one L-malate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one L-malate;

(2R,4aR,10bR)-6-(2,6-Dimethoxy-pyridin-3-yl)-9-ethoxy-8-methoxy-1,2,3,4,4a, 10b-hexahydro-phenanthridin-2-ol fumarate;

(2R,4aR,10bR)-9-Ethoxy-8-methoxy-6-pyrimidin-5-yl-1,2,3,4,4a, 10b-hexahydro-phenanthridin-2-ol fumarate;

(2R,4aR,10bR)-9-Ethoxy-8-methoxy-6-(6-pyrazol-1-yl-pyridin-3-yl)-1,2,3,4,4a, 10b-hexahydro-phenanthridin-2-ol fumarate;

(2R,4aR,10bR)-9-Ethoxy-8-methoxy-6-(2-methoxy-pyrimidin-5-yl)-1,2,3,4,4a, 10b-hexahydro-phenanthridin-2-ol fumarate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol fumarate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol fumarate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol fumarate;

(2R,4aR,10bR)-9-Ethoxy-8-methoxy-6-(6-methoxy-pyridin-3-yl)-1,2,3,4,4a, 10b-hexahydro-phenanthridin-2-ol fumarate;

(2R,4aR,10bR )-6-(2-Dimethylamino-4-methoxy-pyrimidin-5-yl)-9-ethoxy-8-methoxy-1,2,3,4,4a, 10b-hexahydro-phenanthridin-2-ol fumarate;

(2R,4aR,10bR)-6-(4,6-Dimethoxy-pyridin-3-yl)-9-ethoxy-8-methoxy-1,2,3,4,4a, 10b-hexahydro-phenanthridin-2-ol fumarate;

(2R,4aR,10bR)-6-(2-Dimethylamino-pyrimidin-5-yl)-9-ethoxy-8-methoxy-1,2,3,4,4a, 10b-hexahydro-phenanthridin-2-ol fumarate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one fumarate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one fumarate;

(2R,4aR,10bR)-6-(2,6-Dimethoxy-pyridin-3-yl)-9-ethoxy-8-methoxy-1,2,3,4,4a, 10b-hexahydro-phenanthridin-2-ol maleinate;

(2R,4aR,10bR)-9-Ethoxy-8-methoxy-6-pyrimidin-5-yl-1,2,3,4,4a, 10b-hexahydro-phenanthridin-2-ol maleinate;

(2R,4aR,10bR)-9-Ethoxy-8-methoxy-6-(2-methoxy-pyrimidin-5-yl)-1,2,3,4,4a, 10b-hexahydro-phenanthridin-2-ol maleinate;

(2R,4aR,10bR)-6-(2,4-Dimethoxy-pyrimidin-5-yl-9-ethoxy-8-methoxy-1,2,3,4,4a, 10b-hexahydro-phenanthridin-2-ol maleinate;

(2R,4aR,10bR)-9-Ethoxy-8-methoxy-6-pyrazin-2-yl-1,2,3,4,4a, 10b-hexahydro-phenanthridin-2-ol maleinate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol maleinate;
(2R,4aR,10bR)-9-Ethoxy-8-methoxy-6-(6-methoxy-pyridin-3-yl)-1,2,3,4,4a, 10b-hexahydro-phenanthridin-2-ol maleinate;
(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol maleinate;
(2R,4aR,10bR)-6-(4,6-Dimethoxy-pyridin-3-yl)-9-ethoxy-8-methoxy-1,2,3,4,4a, 10b-hexahydro-phenanthridin-2-ol maleinate;
(2R,4aR,10bR)-6-(2-Dimethylamino-pyrimidin-5-yl)-9-ethoxy-8-methoxy-1,2,3,4,4a, 10b-hexahydro-phenanthridin-2-ol maleinate;
5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one maleinate;
5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one maleinate;
(2R,4aR,10bR)-6-(2,6-Dimethoxy-pyridin-3-yl)-9-ethoxy-8-methoxy-1,2,3,4,4a, 10b-hexahydro-phenanthridin-2-ol 2-oxoglutarate;
(2R,4aR,10bR)-9-Ethoxy-8-methoxy-6-pyrimidin-5-yl-1,2,3,4,4a, 10b-hexahydro-phenanthridin-2-ol 2-oxoglutarate;
(2R,4aR,10bR)-9-Ethoxy-8-methoxy-6-(6-pyrazol-1-yl-pyridin-3-yl)-1,2,3,4,4a, 10b-hexahydro-phenanthridin-2-ol 2-oxoglutarate;
(2R,4aR, 10bR)-9-Ethoxy-8-methoxy-6-(2-methoxy-pyrimidin-5-yl)-1,2,3,4,4a, 10b-hexahydro-phenanthridin-2-ol 2-oxoglutarate;
(2R,4aR,10bR)-6-(2,4-Dimethoxy-pyrimidin-5-yl)-9-ethoxy-8-methoxy-1,2,3,4,4a, 10b-hexahydro-phenanthridin-2-ol 2-oxoglutarate;
(2R,4aR,10bR)-9-Ethoxy-6-(6-imidazol-1-yl-pyridin-3-yl)-8-methoxy-1,2,3,4,4a, 10b-hexahydro-phenanthridin-2-ol 2-oxoglutarate;
(2R,4aR,10bR)-9-Ethoxy-8-methoxy-6-pyrazin-2-yl-1,2,3,4,4a, 10b-hexahydro-phenanthridin-2-ol 2-oxoglutarate;
(2R,4aR,10bR)-6-(3,6-Dimethoxy-pyridazin-4-yl)-9-ethoxy-8-methoxy-1,2,3,4,4a, 10b-hexahydro-phenanthridin-2-ol 2-oxoglutarate;
(2R,4aR,10bR)-9-Ethoxy-8-methoxy-6-(6-methoxy-pyridin-3-yl)-1,2,3,4,4a, 10b-hexahydro-phenanthridin-2-ol 2-oxoglutarate;
(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol 2-oxoglutarate;
(2R,4aR,10bR)-6-(4,6-Dimethoxy-pyridin-3-yl)-9-ethoxy-8-methoxy-1,2,3,4,4a, 10b-hexahydro-phenanthridin-2-ol 2-oxoglutarate;
(2R,4aR,10bR)-6-(2-Dimethylamino-pyrimidin-5-yl)-9-ethoxy-8-methoxy-1,2,3,4,4a, 10b-hexahydro-phenanthridin-2-ol 2-oxoglutarate;
5-((2R,4aR,10bR)-9-Ethoxy-2-hydroxy-8-methoxy-1,2,3,4, 4a, 10b-hexahydro-phenanthridin-6-yl)-1-methyl-1H-pyridin-2-one 2-oxoglutarate;
5-((2R,4aR,10bR)-9-Ethoxy-2-hydroxy-8-methoxy-1,2,3,4, 4a, 10b-hexahydro-phenanthridin-6-yl)-1-methyl-1H-pyrimidin-2-one 2-oxoglutarate;
(2R,4aR,10bR)-6-(2,6-Dimethoxy-pyridin-3-yl)-9-ethoxy-8-methoxy-1,2,3,4,4a, 10b-hexahydro-phenanthridin-2-ol oxalate;
(2R,4aR,10bR)-9-Ethoxy-8-methoxy-6-pyrimidin-5-yl-1,2, 3,4,4a, 10b-hexahydro-phenanthridin-2-ol oxalate;
(2R,4aR,10bR)-9-Ethoxy-8-methoxy-6-(2-methoxy-pyrimidin-5-yl)-1,2,3,4,4a, 10b-hexahydro-phenanthridin-2-ol oxalate;
(2R,4aR,10bR)-6-(2,4-Dimethoxy-pyrimidin-5-yl)-9-ethoxy-8-methoxy-1,2,3,4,4a, 10b-hexahydro-phenanthridin-2-ol oxalate;
(2R,4aR,10bR)-9-Ethoxy-6-(6-imidazol-1-yl-pyridin-3-yl)-8-methoxy-1,2,3,4,4a, 10b-hexahydro-phenanthridin-2-ol oxalate;
(2R,4aR,10bR)-6-(3,6-Dimethoxy-pyridazin-4-yl)-9-ethoxy-8-methoxy-1,2,3,4,4a, 10b-hexahydro-phenanthridin-2-ol oxalate;
(2R,4aR,10bR)-6-(4,6-Dimethoxy-pyridin-3-yl)-9-ethoxy-8-methoxy-1,2,3,4,4a, 10b-hexahydro-phenanthridin-2-ol oxalate;
(2R,4aR,10bR)-6-(2-Dimethylamino-pyrimidin-5-yl)-9-ethoxy-8-methoxy-1,2,3,4,4a, 10b-hexahydro-phenanthridin-2-ol oxalate;
5-((2R,4aR,10bR)-9-Ethoxy-2-hydroxy-8-methoxy-1,2,3,4, 4a, 10b-hexahydro-phenanthridin-6-yl)-1-methyl-1H-pyridin-2-one oxalate;
5-((2R,4aR,10bR)-9-Ethoxy-2-hydroxy-8-methoxy-1,2,3,4, 4a, 10b-hexahydro-phenanthridin-6-yl)-1-methyl-1H-pyrimidin-2-one oxalate;
(2R,4aR,10bR)-6-(2,6-Dimethoxy-pyridin-3-yl)-9-ethoxy-8-methoxy-1,2,3,4,4a, 10b-hexahydro-phenanthridin-2-ol D-gluconate;
(2R,4aR,10bR)-9-Ethoxy-8-methoxy-6-pyrimidin-5-yl-1,2, 3,4,4a, 10b-hexahydro-phenanthridin-2-ol D-gluconate;
(2R,4aR,10bR)-9-Ethoxy-8-methoxy-6-(6-pyrazol-1-yl-pyridin-3-yl)-1,2,3,4,4a, 10b-hexahydro-phenanthridin-2-ol D-gluconate;
(2R,4aR,10bR)-9-Ethoxy-8-methoxy-6-(2-methoxy-pyrimidin-5-yl)-1,2,3,4,4a, 10b-hexahydro-phenanthridin-2-ol D-gluconate;
(2R,4aR,10bR)-6-(2,4-Dimethoxy-pyrimidin-5-yl)-9-ethoxy-8-methoxy-1,2,3,4,4a, 10b-hexahydro-phenanthridin-2-ol D-gluconate;
(2R,4aR,10bR)-9-Ethoxy-8-methoxy-6-pyrazin-2-yl-1,2,3, 4,4a, 10-hexahydro-phenanthridin-2-ol D-gluconate;
(2R,4aR,10bR)-6-(3,6-Dimethoxy-pyridazin-4-yl)-9-ethoxy-8-methoxy-1,2,3,4,4a, 10b-hexahydro-phenanthridin-2-ol D-gluconate;
(2R,4aR,10bR)-9-Ethoxy-8-methoxy-6-(6-methoxy-pyridin-3-yl)-1,2,3,4,4a, 10b-hexahydro-phenanthridin-2-ol D-gluconate;
(2R,4aR,10bR )-6-(2-Dimethylamino-4-methoxy-pyrimidin-5-yl)-9-ethoxy-8-methoxy-1,2,3,4,4a, 10b-hexahydro-phenanthridin-2-ol D-gluconate;
(2R,4aR,10bR)-6-(4,6-Dimethoxy-pyridin-3-yl)-9-ethoxy-8-methoxy-1,2,3,4,4a, 10b-hexahydro-phenanthridin-2-ol D-gluconate;
5-((2R,4aR,10bR)-9-Ethoxy-2-hydroxy-8-methoxy-1,2,3,4, 4a, 10b-hexahydro-phenanthridin-6-yl)-1-methyl-1H-pyridin-2-one D-gluconate;
5-((2R,4aR,10bR)-9-Ethoxy-2-hydroxy-8-methoxy-1,2,3,4, 4a, 10b-hexahydro-phenanthridin-6-yl)-1-methyl-1H-pyrimidin-2-one D-gluconate;
(2R,4aR,10bR)-9-Ethoxy-8-methoxy-6-(6-pyrazol-1-yl-pyridin-3-yl)-1,2,3,4,4a, 10b-hexahydro-phenanthridin-2-ol oxalate; and
(2R,4aR,10bR)-9-Ethoxy-8-methoxy-6-pyrazin-2-yl-1,2,3, 4,4a, 10b-hexahydro-phenanthridin-2-ol oxalate.

Further thus, the invention also relates, in a second aspect, to the following salts (2R,4aR,10bR)-6-(5,6-Dimethoxy-pyridin-3-yl)-9-ethoxy-8-methoxy-1,2,3,4,4a,10b-hexahydro-phenanthridin-2-ol hydrochloride;

(2R,4aR,10bR)-9-Ethoxy-8-methoxy-6-(2-methylsulfanyl-pyrimidin-5-yl)-1,2,3,4,4a,10b-hexahydro-phenanthridin-2-ol hydrochloride;

(2R,4aR,10bR)-6-(5,6-Dimethoxy-pyridin-3-yl)-9-ethoxy-8-methoxy-1,2,3,4,4a,10b-hexahydro-phenanthridin-2-ol sulfate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol sulfate;

(2R,4aR,10bR)-9-Ethoxy-8-methoxy-6-(6-methoxy-pyridin-3-yl)-1,2,3,4,4a,10b-hexahydro-phenanthridin-2-ol sulfate;

(2R,4aR,10bR)-6-(5,6-Dimethoxy-pyridin-3-yl)-9-ethoxy-8-methoxy-1,2,3,4,4a,10b-hexahydro-phenanthridin-2-ol methansulfonate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol methansulfonate;

(2R,4aR,10bR)-6-(5,6-Dimethoxy-pyridin-3-yl)-9-ethoxy-8-methoxy-1,2,3,4,4a,10b-hexahydro-phenanthridin-2-ol citrate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol citrate;

(2R,4aR,10bR)-6-(5,6-Dimethoxy-pyridin-3-yl)-9-ethoxy-8-methoxy-1,2,3,4,4a,10b-hexahydro-phenanthridin-2-ol L-tartrate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol L-tartrate;

(2R,4aR,10bR)-6-(5,6-Dimethoxy-pyridin-3-yl)-9-ethoxy-8-methoxy-1,2,3,4,4a,10b-hexahydro-phenanthridin-2-ol D-tartrate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol D-tartrate;

(2R,4aR,10bR)-9-Ethoxy-8-methoxy-6-(6-methoxy-pyridin-3-yl)-1,2,3,4,4a,10b-hexahydro-phenanthridin-2-ol D-tartrate;

(2R,4aR,10bR)-6-(5,6-Dimethoxy-pyridin-3-yl)-9-ethoxy-8-methoxy-1,2,3,4,4a,10b-hexahydro-phenanthridin-2-ol meso-tartrate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol meso-tartrate;

(2R,4aR,10bR)-9-Ethoxy-8-methoxy-6-(6-methoxy-pyridin-3-yl)-1,2,3,4,4a,10b-hexahydro-phenanthridin-2-ol meso-tartrate;

(2R,4aR,10bR)-6-(5,6-Dimethoxy-pyridin-3-yl)-9-ethoxy-8-methoxy-1,2,3,4,4a,10b-hexahydro-phenanthridin-2-ol D-malate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol D-malate;

(2R,4aR,10bR)-9-Ethoxy-8-methoxy-6-(6-methoxy-pyridin-3-yl)-1,2,3,4,4a,10b-hexahydro-phenanthridin-2-ol D-malate;

(2R,4aR,10bR)-6-(5,6-Dimethoxy-pyridin-3-yl)-9-ethoxy-8-methoxy-1,2,3,4,4a,10b-hexahydro-phenanthridin-2-ol L-malate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol L-malate;

(2R,4aR,10bR)-9-Ethoxy-8-methoxy-6-(6-methoxy-pyridin-3-yl)-1,2,3,4,4a,10b-hexahydro-phenanthridin-2-ol L-malate;

(2R,4aR,10bR)-6-(5,6-Dimethoxy-pyridin-3-yl)-9-ethoxy-8-methoxy-1,2,3,4,4a,10b-hexahydro-phenanthridin-2-ol fumarate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol fumarate;

(2R,4aR,10bR)-6-(5,6-Dimethoxy-pyridin-3-yl)-9-ethoxy-8-methoxy-1,2,3,4,4a,10b-hexahydro-phenanthridin-2-ol maleinate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol maleinate;

(2R,4aR,10bR)-6-(5,6-Dimethoxy-pyridin-3-yl)-9-ethoxy-8-methoxy-1,2,3,4,4a,10b-hexahydro-phenanthridin-2-ol oxoglutarate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol oxoglutarate;

(2R,4aR,10bR)-6-(2,6-Dimethoxy-pyridin-3-yl)-9-ethoxy-8-methoxy-1,2,3,4,4a,10b-hexahydro-phenanthridin-2-ol edisilate;

(2R,4aR,10bR)-9-Ethoxy-8-methoxy-6-pyrimidin-5-yl-1,2,3,4,4a,10b-hexahydro-phenanthridin-2-ol edisilate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol edisilate;

(2R,4aR,10bR)-9-Ethoxy-8-methoxy-6-(2-methoxy-pyrimidin-5-yl)-1,2,3,4,4a,10b-hexahydro-phenanthridin-2-ol edisilate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol edisilate;

(2R,4aR,10bR)-9-Ethoxy-6-(6-imidazol-1-yl-pyridin-3-yl)-8-methoxy-1,2,3,4,4a,10b-hexahydro-phenanthridin-2-ol edisilate;

(2R,4aR,10bR)-9-Ethoxy-8-methoxy-6-pyrazin-2-yl-1,2,3,4,4a,10b-hexahydro-phenanthridin-2-ol edisilate;

(2R,4aR,10bR)-6-(3,6-Dimethoxy-pyridazin-4-yl)-9-ethoxy-8-methoxy-1,2,3,4,4a,10b-hexahydro-phenanthridin-2-ol edisilate;

(2R,4aR,10bR)-9-Ethoxy-8-methoxy-6-(6-methoxy-pyridin-3-yl)-1,2,3,4,4a,10b-hexahydro-phenanthridin-2-ol edisilate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol edisilate;

(2R,4aR,10bR)-6-(4,6-Dimethoxy-pyridin-3-yl)-9-ethoxy-8-methoxy-1,2,3,4,4a,10b-hexahydro-phenanthridin-2-ol edisilate;

(2R,4aR,10bR)-6-(2-Dimethylamino-pyrimidin-5-yl)-9-ethoxy-8-methoxy-1,2,3,4,4a,10b-hexahydro-phenanthridin-2-ol edisilate;

(2R,4aR,10bR)-6-(5,6-Dimethoxy-pyridin-3-yl)-9-ethoxy-8-methoxy-1,2,3,4,4a,10b-hexahydro-phenanthridin-2-ol edisilate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol edisilate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one edisilate;

5-((2R,4aR,10bR)-9-Ethoxy-2-hydroxy-8-methoxy-1,2,3,4,4a,10b-hexahydro-phenanthridin-4-yl)-1-methyl-1H-pyrimidin-2-one edisilate;

(2R,4aR,10bR)-6-(2,6-Dimethoxy-pyridin-3-yl)-9-ethoxy-8-methoxy-1,2,3,4,4a,10b-hexahydro-phenanthridin-2-ol esilate;

(2R,4aR,10bR)-9-Ethoxy-8-methoxy-6-pyrimidin-5-yl-1,2,3,4,4a,10b-hexahydro-phenanthridin-2-ol esilate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol esilate;

(2R,4aR,10bR)-9-Ethoxy-8-methoxy-6-(2-methoxy-pyrimidin-5-yl)-1,2,3,4,4a,10b-hexahydro-phenanthridin-2-ol esilate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol esilate;

(2R,4aR,10bR)-9-Ethoxy-6-(6-imidazol-1-yl-pyridin-3-yl)-8-methoxy-1,2,3,4,4a,10b-hexahydro-phenanthridin-2-ol esilate;

(2R,4aR,10bR)-9-Ethoxy-8-methoxy-6-pyrazin-2-yl-1,2,3,4,4a,10b-hexahydro-phenanthridin-2-ol esilate;

(2R,4aR,10bR)-6-(3,6-Dimethoxy-pyridazin-4-yl)-9-ethoxy-8-methoxy-1,2,3,4,4a,10b-hexahydro-phenanthridin-2-ol esilate;

(2R,4aR,10bR)-9-Ethoxy-8-methoxy-6-(6-methoxy-pyridin-3-yl)-1,2,3,4,4a,10b-hexahydro-phenanthridin-2-ol esilate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol esilate;

(2R,4aR,10bR)-6-(4,6-Dimethoxy-pyridin-3-yl)-9-ethoxy-8-methoxy-1,2,3,4,4a,10b-hexahydro-phenanthridin-2-ol esilate;

(2R,4aR,10bR)-6-(2-Dimethylamino-pyrimidin-5-yl)-9-ethoxy-8-methoxy-1,2,3,4,4a,10b-hexahydro-phenanthridin-2-ol esilate;

(2R,4aR,10bR)-6-(5,6-Dimethoxy-pyridin-3-yl)-9-ethoxy-8-methoxy-1,2,3,4,4a,10b-hexahydro-phenanthridin-2-ol esilate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol esilate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one esilate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one esilate;

(2R,4aR,10bR)-6-(2,6-Dimethoxy-pyridin-3-yl)-9-ethoxy-8-methoxy-1,2,3,4,4a,10b-hexahydro-phenanthridin-2-ol hydrobromide;

(2R,4aR,10bR)-9-Ethoxy-8-methoxy-6-pyrimidin-5-yl-1,2,3,4,4a,10b-hexahydro-phenanthridin-2-ol hydrobromide;

(2R,4aR,10bR)-9-Ethoxy-8-methoxy-6-(6-pyrazol-1-yl-pyridin-3-yl)-1,2,3,4,4a,10b-hexahydro-phenanthridin-2-ol hydrobromide;

(2R,4aR,10bR)-9-Ethoxy-8-methoxy-6-(2-methoxy-pyrimidin-5-yl)-1,2,3,4,4a,10b-hexahydro-phenanthridin-2-ol hydrobromide;

(2R,4aR,10bR)-6-(2,4-Dimethoxy-pyrimidin-5-yl)-9-ethoxy-8-methoxy-1,2,3,4,4a,10b-hexahydro-phenanthridin-2-ol hydrobromide;

(2R,4aR,10bR)-9-Ethoxy-6-(6-imidazol-1-yl-pyridin-3-yl)-8-methoxy-1,2,3,4,4a,10b-hexahydro-phenanthridin-2-ol hydrobromide;

(2R,4aR,10bR)-9-Ethoxy-8-methoxy-6-pyrazin-2-yl-1,2,3,4,4a,10b-hexahydro-phenanthridin-2-ol hydrobromide;

(2R,4aR,10bR)-6-(3,6-Dimethoxy-pyridazin-4-yl)-9-ethoxy-8-methoxy-1,2,3,4,4a,10b-hexahydro-phenanthridin-2-ol hydrobromide;

(2R,4aR,10bR)-9-Ethoxy-8-methoxy-6-(6-methoxy-pyridin-3-yl)-1,2,3,4,4a,10b-hexahydro-phenanthridin-2-ol hydrobromide;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol hydrobromide;

(2R,4aR,10bR)-6-(4,6-Dimethoxy-pyridin-3-yl)-9-ethoxy-8-methoxy-1,2,3,4,4a,10b-hexahydro-phenanthridin-2-ol hydrobromide;

(2R,4aR,10bR)-6-(2-Dimethylamino-pyrimidin-5-yl)-9-ethoxy-8-methoxy-1,2,3,4,4a,10b-hexahydro-phenanthridin-2-ol hydrobromide;

(2R,4aR,10bR)-6-(5,6-Dimethoxy-pyridin-3-yl)-9-ethoxy-8-methoxy-1,2,3,4,4a,10b-hexahydro-phenanthridin-2-ol hydrobromide;

(2R,4aR,10bR)-9-Ethoxy-8-methoxy-6-(2-methylsulfanyl-pyrimidin-5-yl)-1,2,3,4,4a,10b-hexahydro-phenanthridin-2-ol hydrobromide;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one hydrobromide;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one hydrobromide;

(2R,4aR,10bR)-6-(2,6-Dimethoxy-pyridin-3-yl)-9-ethoxy-8-methoxy-1,2,3,4,4a,10b-hexahydro-phenanthridin-2-ol tosylate;

(2R,4aR,10bR)-9-Ethoxy-8-methoxy-6-pyrimidin-5-yl-1,2,3,4,4a,10b-hexahydro-phenanthridin-2-ol tosylate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol tosylate;

(2R,4aR,10bR)-9-Ethoxy-8-methoxy-6-(2-methoxy-pyrimidin-5-yl)-1,2,3,4,4a,10b-hexahydro-phenanthridin-2-ol tosylate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol tosylate;

(2R,4aR,10bR)-9-Ethoxy-6-(6-imidazol-1-yl-pyridin-3-yl)-8-methoxy-1,2,3,4,4a,10b-hexahydro-phenanthridin-2-ol tosylate;

(2R,4aR,10bR)-9-Ethoxy-8-methoxy-6-pyrazin-2-yl-1,2,3,4,4a,10b-hexahydro-phenanthridin-2-ol tosylate;

(2R,4aR,10bR)-6-(3,6-Dimethoxy-pyridazin-4-yl)-9-ethoxy-8-methoxy-1,2,3,4,4a,10b-hexahydro-phenanthridin-2-ol tosylate;

(2R,4aR,10bR)-9-Ethoxy-8-methoxy-6-(6-methoxy-pyridin-3-yl)-1,2,3,4,4a,10b-hexahydro-phenanthridin-2-ol tosylate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol tosylate;

(2R,4aR,10bR)-6-(4,6-Dimethoxy-pyridin-3-yl)-9-ethoxy-8-methoxy-1,2,3,4,4a,10b-hexahydro-phenanthridin-2-ol tosylate;

(2R,4aR,10bR)-6-(2-Dimethylamino-pyrimidin-5-yl)-9-ethoxy-8-methoxy-1,2,3,4,4a,10b-hexahydro-phenanthridin-2-ol tosylate;

(2R,4aR,10bR)-6-(5,6-Dimethoxy-pyridin-3-yl)-9-ethoxy-8-methoxy-1,2,3,4,4a,10b-hexahydro-phenanthridin-2-ol tosylate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol tosylate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one tosylate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one tosylate;

(2R,4aR,10bR)-6-(5,6-Dimethoxy-pyridin-3-yl)-9-ethoxy-8-methoxy-1,2,3,4,4a, 10b-hexahydro-phenanthridin-2-ol oxalate;

(2R,4aR,10bR)-9-Ethoxy-8-methoxy-6-(2-methylsulfanyl-pyridin-5-yl)-1,2,3,4,4a, 10b-hexahydro-phenanthridin-2-ol oxalate;

(2R,4aR,10bR)-9-Ethoxy-8-methoxy-6-(6-methoxy-pyridin-3-yl)-1,2,3,4,4a, 10b-hexahydro-phenanthridin-2-ol oxalate;

(2R,4aR,10bR)-6-(5,6-Dimethoxy-pyridin-3-yl)-9-ethoxy-8-methoxy-1,2,3,4,4a, 10b-hexahydro-phenanthridin-2-ol D-gluconate; and (2R,4aR,10bR)-9-Ethoxy-8-methoxy-6-(2-methylsulfanyl-pyrimidin-5-yl)-1,2,3,4,4a,10b-hexahydro-phenanthridin-2-ol D-gluconate.

It is known to the person skilled in the art that compounds, when they are isolated, for example, in crystalline form, can contain various amounts of solvents. The invention therefore also comprises all solvates and in particular all hydrates of the compounds according to this invention.

Furthermore, the invention includes all conceivable tautomeric forms of the compounds of the present invention in pure form as well as any mixtures thereof.

Furthermore, the invention includes all conceivable polymorphic forms of the compounds of the present invention in pure form as well as any mixtures thereof.

The compounds according to the invention and their starting compounds can be prepared, for example, in a manner as described by way of example in the following examples, or analogously or similarly thereto, or as described in the International application WO2005/085225 (PCT/EP2005/050931) the disclosure of which is incorporated herein.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as methanol, ethanol or isopropanol) which contains the desired acid, or to which the desired acid is then added. The salts are obtained by filtering, reprecipitating, precipitating with a nonsolvent for the addition salt or by evaporating the solvent. Salts obtained can be converted into the free compounds, which can in turn be converted into salts, by acidification. In this manner, pharmacologically unacceptable salts can be converted into pharmacologically acceptable salts.

Optionally the salts according to this invention can be converted in a suitable solvent with the aid of a suitable base into the free compounds, which can be isolated in a manner known per se.

The solvates or particularly hydrates of the compounds according to this invention can be prepared in a manner known per se, e.g. in the presence of the appropriate solvent. Hydrates may be obtained from water or from mixtures of water with polar organic solvents (for example alcohols, e.g. methanol, ethanol or isopropanol, or ketones, e.g. acetone).

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds according to this invention. All these other possible synthesis routes are also part of this invention.

The present invention also relates to intermediates, including their salts, methods and processes useful in synthesizing compounds according to this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims.

The examples below illustrate the invention in more detail, without limiting it. Any or all of the compounds according to this invention which are mentioned as final compounds in the following examples are a preferred subject of the present invention.

In the examples, m.p. stands for melting point, h for hour(s), min for minutes, $R_f$ for rentention factor in thin layer chromatography, s.p. for sintering point, EF for empirical formula, MW for molecular weight, MS for mass spectrum, M for molecular ion, fnd. for found, calc. for calculated, other abbreviations have their meanings customary per se to the skilled person.

According to common practice in stereochemistry, the symbols RS and SR are used to denote the specific configuration of each of the chiral centers of a racemate. In more detail, for example, the term "(2RS,4aRS,10bRS)" stands for a racemate (racemic mixture) comprising the one enantiomer having the configuration (2R,4aR,10bR) and the other enantiomer having the configuration (2S,4aS,10bS).

EXAMPLES

Final Compounds

Starting from the appropriate free bases mentioned below (compounds 2 to 17) and the appropriate acid the corresponding salts can be obtained, for example, according to the following general procedure, or analogously or similarly thereto:

About 1 g of the free base is solved in about 10 ml of a suitable solvent at room temperature or at elevated temperature. To this solution about 1.1 eq. of the appropriate acid is added in one portion under stirring. The mixture is stirred over night while the salt precipitates. The salt is filtered off, washed with about 2 ml of a suitable solvent and dried over night at about 50° C. in vacuo. Suitable solvents may include, without being restricted thereto, organic solvents, such as, for example, lower alcohols (e.g. methanol, ethanol, isopropanol or the like), ether solvents (e.g. THF, dioxane, di-ethylether or the like) or ketone solvents (e.g. acetone, methyl isobutyl ketone or the like), as well as mixtures of organic solvents, or mixtures thereof with water, or water, with or without heating. Thus, for example, in the case of hydrochloric acid or hydrobromic acid an ether or alcohol or ketone solvent (e.g. dioxane, THF, diethylether, methanol, ethanol, isopropanol, methyl isobutyl ketone or the like), or in the case of organic acids, such as e.g. fumaric, tartaric, 2-oxoglutaric acid or a sulfonic acid or the like, a ketone solvent (e.g. acetone or methyl isobutyl ketone), an ether solvent (e.g. THF) or an alcohol solvent (e.g. isopropanol) may be suitable.

Representative Example

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol 2-oxoglutarate

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol ((42.7 mg, 0.1 mmol) are dissolved in 0.5 ml of acetone. 16.1 mg (0.11 mmol) of 2-oxo-pentanedioic acid (dissolved in 0.5 ml of acetone) are added. The crystals are filtered off and dried to obtain 40.6 mg (71%) of the title compound (m.p.: 124° C.).

Further Representative Example

(2R,4aR,10bR)-9-Ethoxy-8-methoxy-6-(6-pyrazol-1-yl-pyridin-3-yl)-1,2,3,4,4a, 10b-hexahydro-phenanthridin-2-ol fumarate

(2R,4aR,10bR)-9-Ethoxy-8-methoxy-6-(6-pyrazol-1-yl-pyridin-3-yl)-1,2,3,4,4a, 10b-hexahydro-phenanthridin-2-ol (41.9 mg, 0.1 mmol) are dissolved in 0.5 ml of acetone. 12.8 mg (0.11 mmol) of fumaric acid (dissolved in 0.5 ml of a 82:18 mixture of acetone and isopropanol) are added. The crystals are filtered off and dried to obtain 15.4 mg (29%) of the title compound (m. p.: 170° C.).

Further Representative Example

(2R,4aR,10bR)-9-Ethoxy-8-methoxy-6-(2-methoxy-pyrimidin-5-yl)-1,2,3,4,4a, 10b-hexahydro-phenanthridin-2-ol fumurate

(2R,4aR,10bR)-9-Ethoxy-8-methoxy-6-(2-methoxy-pyrimidin-5-yl)-1,2,3,4,4a, 10b-hexahydro-phenanthridin-2-ol (38.3 mg, 0.1 mmol) are dissolved in 0.5 ml of acetone. 12.8 mg (0.11 mmol) of fumaric acid (dissolved in 0.5 ml of a 82:18 mixture of acetone and isopropanol) are added. The crystals are filtered off and dried to obtain 32.1 mg (64%) of the title compound (m. p.: 124° C.).

Further Representative Example

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol L-tartrate

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol (42.7 mg, 0.1 mmol) are dissolved in 0.5 ml of acetone. 16.5 mg (0.11 mmol) of L-tartaric acid (dissolved in 0.5 ml of a 75:15 mixture of acetone and isopropanol) are added. The crystals are filtered off and dried to obtain 42.9 mg (74%) of the title compound (m. p.: 249° C.).

Further Representative Example

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol fumarate

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol (42.7 mg, 0.1 mmol) are dissolved in 0.5 ml of acetone. 12.8 mg (0.11 mmol) of fumaric acid (dissolved in 0.5 ml of a 82:18 mixture of acetone and isopropanol) are added. The crystals are filtered off and dried to obtain 30.9 mg (57%) of the Utle compound (m. p.: 123° C.).

Further Representative Example

(2R,4aR,10bR)-6-(2,6-Dimethoxy-pyridin-3-yl)-9-ethoxy-8-methoxy-1,2,3,4,4a, 10b-hexahydro-phenanthridin-2-ol hydrobromide

(2R,4aR,10bR)-6-(2,6-Dimethoxy-pyridin-3-yl)-9-ethoxy-8-methoxy-1,2,3,4,4a, 10b-hexahydro-phenanthridin-2-ol (1.2 g; 2.9 mmol) is dissolved in 7.2 ml of 4-methyl-2-pentanone. The solution is heated up to 60° C. 350 µl (3.05 mmol) of aqueous HBr (W=47%) are added. After crystallisation the suspension is stirred over night. The crystals are filtered off and dried to obtain 1.38 g (97%) of the title compound (m.p.: 163° C.).

Further Representative Example

(2R,4aR,10bR)-6-(2,6-Dimethoxy-pyridin-3-yl)-9-ethoxy-8-methoxy-1,2,3,4,4a, 10b-hexahydro-phenanthridin-2-ol mesylate

(2R,4aR,10bR)-6-(2,6-Dimethoxy-pyridin-3-yl)-9-ethoxy-8-methoxy-1,2,3,4,4a, 10b-hexahydro-phenanthridin-2-ol (1.5 g; 3.6 mmol) is dissolved in 9 ml of tetrahydrofuran. The solution is heated up to 60° C. 247 µg (3.8 mmol) of methanesulfonic acid are added. After crystallisation the suspension is stirred over night. The crystals are filtered off and dried to obtain 1.73 g (95%) of the title compound (m.p.: 193° C.).

Further Representative Example

(2R,4aR,10bR)-6-(4,6-Dimethoxy-pyridin-3-yl)-9-ethoxy-8-methoxy-1,2,3,4,4a, 10b-hexahydro-phenanthridin-2-ol fumarate

(2R,4aR,10bR)-6-(4,6-Dimethoxy-pyridin-3-yl)-9-ethoxy-8-methoxy-1,2,3,4,4a, 10b-hexahydro-phenanthridin-2-ol (41.2 mg, 0.1 mmol) are dissolved in 0.5 ml of acetone. 12.8 mg (0.11 mmol) of fumaric acid (dissolved in 0.5 ml of a 82:18 mixture of acetone and isopropanol) are added. The crystals are filtered off and dried to obtain 21.1 mg (40%) of the title compound (m. p.: 194° C.).

Further Representative Example

(2R,4aR,10bR)-6-(2-Dimethylamino-pyrimidin-5-yl)-9-ethoxy-8-methoxy-1,2,3,4,4a, 10b-hexahydro-phenanthridin-2-ol 2-oxoglutarate

(2R,4aR,10bR)-6-(2-Dimethylamino-pyrimidin-5-yl)-9-ethoxy-8-methoxy-1,2,3,4,4a, 10b-hexahydro-phenanthridin-2-ol (39.4 mg, 0.1 mmol) are dissolved in 1.0 ml of dichloromethane. 16.1 mg (0.11 mmol) of 2-oxo-pentanedioic acid (dissolved in 0.5 ml of acetone) are added. The crystals are filtered off and dried to obtain 30.9 mg (57%) of the title compound (m. p.: 112° C.).

Further Representative Example (2R,4aR,10bR)-6-(2,6-Dimethoxy-pyridin-3-yl)-9-ethoxy-8-methoxy-1,2,3,4,4a, 10b-hexahydro-phenanthridin-2-ol hydrochloride (2R,4aR,10bR)-6-(2,6-Dimethoxy-pyridin-3-yl)-9-ethoxy-8-methoxy-1,2,3,4,4a, 10b-hexahydro-phenanthridin-2-ol (1.5 g; 3.6 mmol) is dissolved in 9 ml of 2-propanol. The solution is heated up to 60° C. 760 µl (3.8 mmol) of HCl (c=5 mol/l in 2-propanol) are added. The solution is cooled down to room temperature and stirred over night. The solution is inoculated with some crystals of the title compound. After crystallisation the suspension is stirred over night. The crystals are filtered off and dried to obtain 0.3 g (19%) of the title compound (m.p.: 164° C.).

Further Representative Example (2R,4aR,10bR)-6-(2,6-Dimethoxy-pyridin-3-yl)-9-ethoxy-8-methoxy-1,2,3,4,4a, 10b-hexahydro-phenanthridin-2-ol ethandisulfonate (2R,4aR,10bR)-6-(2,6-Dimethoxy-pyridin-3-yl)-9-ethoxy-8-methoxy-1,2,3,4,4a, 10b-hexahydro-phenanthridin-2-ol (1.2 g; 2.9 mmol) is dissolved in 8.2 ml of tetrahydrofuran. The solution is heated up to 50° C. 580 mg (3.05 mmol) of ethandisulfonic acid are added. After crystallisation 1 ml ethanol is added and the suspension is stirred over night. The crystals are filtered off and dried to obtain 1.35 g (77%) of the title compound (m.p.: 233° C.).

Further Representative Example (2R,4aR,10bR)-6-(2,6-Dimethoxy-pyridin-3-yl)-9-ethoxy-8-methoxy-1,2,3,4,4a, 10b-hexahydro-phenanthridin-2-ol ethansulfonate (2R,4aR,10bR)-6-(2,6-Dimethoxy-pyridin-3-yl)-9-ethoxy-8-methoxy-1,2,3,4,4a, 10b-hexahydro-phenanthridin-2-ol (1.5 g; 3.64 mmol) is dissolved in 9 ml of 4-methyl-2-pentanone. The solution is heated up to 50° C. 312 µl (3.82 mmol) of ethansulfonic acid are added. After crystallisation 3 ml 4-methyl-2-pentanon is added and the suspension is stirred over night. The crystals are filtered off and dried to obtain 1.78 g (94%) of the title compound (m.p.: 216° C.).

Further Representative Example (2R,4aR,10bR)-6-(2-Dimethylamino-pyrimidin-5-yl)-9-ethoxy-8-methoxy-1,2,3,4,4a, 10b-hexahydro-phenanthridin-2-ol L-tartrate (2R,4aR,10bR)-6-(2-Dimethylamino-pyrimidin-5-yl)-9-ethoxy-8-methoxy-1,2,3,4,4a, 10b-hexahydro-phenanthridin-2-ol (42.7 mg, 0.1 mmol) are dissolved in 1.0 ml of dichloromethane. 16.5 mg (0.11 mmol) of L-tartaric acid (dissolved in 0.5 ml of a 75:15 mixture of acetone and isopropanol) are added. The crystals are filtered off and dried to obtain 33.3 mg (61%) of the title compound (m. p.: 206° C.).

Further Representative Example (2R,4aR,10bR)-6-(2-Dimethylamino-pyrimidin-5-yl)-9-ethoxy-8-methoxy-1,2,3,4,4a, 10b-hexahydro-phenanthridin-2-ol fumarate (2R,4aR,10bR)-6-(2-Dimethylamino-pyrimidin-5-yl)-9-ethoxy-8-methoxy-1,2,3,4,4a, 10b-hexahydro-phenanthridin-2-ol (39.4 mg, 0.1 mmol) are dissolved in 1.0 ml of dichloromethane. 12.8 mg (0.11 mmol) of fumaric acid (dissolved in 0.5 ml of a 82:18 mixture of acetone and isopropanol) are added. The crystals are filtered off and dried to obtain 22.9 mg (45%) of the title compound (m. p.: 210° C.).

Further Representative Example (2R,4aR,10bR)-6-(2,6-Dimethoxy-pyridin-3-yl)-9-ethoxy-8-methoxy-1,2,3,4,4a, 10b-hexahydro-phenanthridin-2-ol tosylate (2R,4aR,10bR)-6-(2,6-Dimethoxy-pyridin-3-yl)-9-ethoxy-8-methoxy-1,2,3,4,4a, 10b-hexahydro-phenanthridin-2-ol (1.5 g; 3.6 mmol) is dissolved in 9 ml of 2-propanol. The solution is heated up to 60° C. 723 mg (3.8 mmol) of p-toluenesulfonic acid are added. The solution is cooled down to room temperature and stirred over night. From a part of the solution seed crystals are produced and added to the remaining solution. The crystals are filtered off and dried to obtain 1.98 g (94%) of the title compound (m.p.: 218° C.).

Further Representative Example 5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one 2-oxoglutarate 5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one (38.2 mg, 0.1 mmol) are dissolved in 0.5 ml of acetone. 16.1 mg (0.11 mmol) of 2-oxo-pentanedioic acid (dissolved in 0.5 ml of acetone) are added. The crystals are filtered off and dried to obtain 35.3 mg (67%) of the titlee compound (m. p.: 147° C.).

Further Representative Example 5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one L-tartrate 5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one (38.2 mg, 0.1 mmol) are dissolved in 0.5 ml of acetone. 16.5 mg (0.11 mmol) of L-tartaric acid (dissolved in 0.5 ml of a 75:15 mixture of acetone and isopropanol) are added. The crystals are filtered off and dried to obtain 44.2 mg (83%) of the title compound (m. p.: 205° C.).

Further Representative Example 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one fumarate 5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one (38.2 mg, 0.1 mmol) are dissolved in 0.5 ml of acetone. 12.8 mg (0.11 mmol) of fumaric acid (dissolved in 0.5 ml of a 82:18 mixture of acetone and isopropanol) are added. The crystals are filtered off and dried to obtain 25.6 mg (51%) of the title compound (m. p.: 156° C.).

Further Representative Example (2R,4aR,10bR)-9-Ethoxy-8-methoxy-6-(6-methoxy-pyridin-3-yl)-1,2,3,4,4a, 10b-hexahydro-phenanthridin-2-ol fumarate (2R,4aR,10bR)-9-Ethoxy-8-methoxy-6-(6-methoxy-pyridin-3-yl)-1,2,3,4,4a, 10b-hexahydro-phenanthridin-2-ol (38.2 mg, 0.1 mmol) are dissolved in 0.5 ml of acetone. 12.8 mg (0.11 mmol) of fumaric acid (dissolved in 0.5 ml of a 82:18 mixture of acetone and isopropanol) are added. The crystals are filtered off and dried to obtain 26.0 mg (52%) of the title compound (m. p.: 173° C.).

The following salts may be obtained according to any of the abovementioned procedures or analogously or similarly thereto:

(2R,4aR,10bR)-6-(2,6-Dimethoxy-pyridin-3-yl)-9-ethoxy-8-methoxy-1,2,3,4,4a, 10b-hexahydro-phenanthridin-2-ol hydrochloride;

(2R,4aR,10bR)-9-Ethoxy-8-methoxy-6-pyrimidin-5-yl-1,2,3,4,4a, 10b-hexahydro-phenanthridin-2-ol hydrochloride;

(2R,4aR,10bR)-9-Ethoxy-8-methoxy-6-(6-pyrazol-1-yl-pyridin-3-yl)-1,2,3,4,4a, 10b-hexahydro-phenanthridin-2-ol hydrochloride;

(2R,4aR,10bR)-9-Ethoxy-8-methoxy-6-(2-methoxy-pyrimidin-5-yl)-1,2,3,4,4a, 10b-hexahydro-phenanthridin-2-ol hydrochloride;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol hydrochloride;

(2R,4aR,10bR)-9-Ethoxy-8-methoxy-6-pyrazin-2-yl-1,2,3,4,4a, 10b-hexahydro-phenanthridin-2-ol hydrochloride;

(2R,4aR,10bR)-6-(3,6-Dimethoxy-pyridazin-4-yl)-9-ethoxy-8-methoxy-1,2,3,4,4a, 10b-hexahydro-phenanthridin-2-ol hydrochloride;

(2R,4aR,10bR)-9-Ethoxy-8-methoxy-6-(6-methoxy-pyridin-3-yl)-1,2,3,4,4a, 10b-hexahydro-phenanthridin-2-ol hydrochloride;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol hydrochloride;

(2R,4aR,10bR)-6-(4,6-Dimethoxy-pyridin-3-yl)-9-ethoxy-8-methoxy-1,2,3,4,4a, 10b-hexahydro-phenanthridin-2-ol hydrochloride;

(2R,4aR,10bR)-6-(2-Dimethylamino-pyrimidin-5-yl)-9-ethoxy-8-methoxy-1,2,3,4,4a, 10b-hexahydro-phenanthridin-2-ol hydrochloride;

(2R,4aR,10bR)-6-(5,6-Dimethoxy-pyridin-3-yl)-9-ethoxy-8-methoxy-1,2,3,4,4a,10b-hexahydro-phenanthridin-2-ol hydrochloride;

(2R,4aR,10bR)-9-Ethoxy-8-methoxy-6-(2-methylsulfanyl-pyrimidin-5-yl)-1,2,3,4,4a, 10b-hexahydro-phenanthridin-2-ol hydrochloride;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one hydrochloride;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one hydrochloride;

(2R,4aR,10bR)-6-(2,6-Dimethoxy-pyridin-3-yl)-9-ethoxy-8-methoxy-1,2,3,4,4a, 10b-hexahydro-phenanthridin-2-ol sulfate;

(2R,4aR,10bR)-9-Ethoxy-8-methoxy-6-(2-methoxy-pyrimidin-5-yl)-1,2,3,4,4a, 10b-hexahydro-phenanthridin-2-ol sulfate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol sulfate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol sulfate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol sulfate;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol sulfate;

(2R,4aR,10bR)-6-(4,6-Dimethoxy-pyridin-3-yl)-9-ethoxy-8-methoxy-1,2,3,4,4a, 10b-hexahydro-phenanthridin-2-ol sulfate;

(2R,4aR,10bR)-6-(2-Dimethylamino-pyrimidin-5-yl)-9-ethoxy-8-methoxy-1,2,3,4,4a, 10b-hexahydro-phenanthridin-2-ol sulfate;

(2R,4aR,10bR)-6-(5,6-Dimethoxy-pyridin-3-yl)-9-ethoxy-8-methoxy-1,2,3,4,4a, 10b-hexahydro-phenanthridin-2-ol sulfate;

(2R,4aR,10bR)-9-Ethoxy-8-methoxy-6-(2-methylsulfanyl-pyrimidin-5-yl)-1,2,3,4,4a, 10b-hexahydro-phenanthridin-2-ol sulfate;

(2R,4aR,10bR)-9-Ethoxy-8-methoxy-6-(6-methoxy-pyridin-3-yl)-1,2,3,4,4a, 10b-hexahydro-phenanthridin-2-ol sulfate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one sulfate;

(2R,4aR,10bR)-6-(2,6-Dimethoxy-pyridin-3-yl)-9-ethoxy-8-methoxy-1,2,3,4,4a, 10b-hexahydro-phenanthridin-2-ol methansulfonate;

(2R,4aR,10bR)-9-Ethoxy-8-methoxy-6-pyrimidin-5-yl-1,2,3,4,4a, 10b-hexahydro-phenanthridin-2-ol methansulfonate;

(2R,4aR,10bR)-9-Ethoxy-8-methoxy-6-(2-methoxy-pyrimidin-5-yl)-1,2,3,4,4a, 10b-hexahydro-phenanthridin-2-ol methansulfonate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol methansulfonate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol methansulfonate;

(2R,4aR,10bR)-9-Ethoxy-8-methoxy-6-pyrazin-2-yl-1,2,3,4,4a, 10b-hexahydro-phenanthridin-2-ol methansulfonate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol methansulfonate;

(2R,4aR,10bR)-9-Ethoxy-8-methoxy-6-(6-methoxy-pyridin-3-yl)-1,2,3,4,4a, 10b-hexahydro-phenanthridin-2-ol methansulfonate;

(2R,4aR,10bR)-6-(2-Dimethylamino-4-methoxy-pyrimidin-5-y)-9-ethoxy-8-methoxy-1,2,3,4,4a, 10b-hexahydro-phenanthridin-2-ol methansulfonate;

(2R,4aR,10bR)-6-(4,6-Dimethoxy-pyridin-3-yl)-9-ethoxy-8-methoxy-1,2,3,4,4a, 10b-hexahydro-phenanthridin-2-ol methansulfonate;

(2R,4aR,10bR)-6-(2-Dimethylamino-pyrimidin-5-yl)-9-ethoxy-8-methoxy-1,2,3,4,4a, 10b-hexahydro-phenanthridin-2-ol methansulfonate;

(2R,4aR,10bR)-6-(5,6-Dimethoxy-pyridin-3-yl)-9-ethoxy-8-methoxy-1,2,3,4,4a, 10b-hexahydro-phenanthridin-2-ol methansulfonate;

(2R,4aR,10bR)-9-Ethoxy-8-methoxy-6-(2-methylsulfanyl-pyrimidin-5-yl)-1,2,3,4,4a, 10b-hexahydro-phenanthridin-2-ol methansulfonate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one methansulfonate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one methansulfonate;

(2R,4aR,10bR)-6-(2,6-Dimethoxy-pyridin-3-yl)-9-ethoxy-8-methoxy-1,2,3,4,4a, 10b-hexahydro-phenanthridin-2-ol citrate;

(2R,4aR,10bR)-9-Ethoxy-8-methoxy-6-(6-pyrazol-1-yl-pyridin-3-yl)-1,2,3,4,4a, 10b-hexahydro-phenanthridin-2-ol citrate;

(2R,4aR,10bR)-9-Ethoxy-8-methoxy-6-(2-methoxy-pyrimidin-5-yl)-1,2,3,4,4a, 10b-hexahydro-phenanthridin-2-ol citrate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol citrate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol citrate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol citrate;

(2R,4aR,10bR)-9-Ethoxy-8-methoxy-6-(6-methoxy-pyridin-3-yl)-1,2,3,4,4a, 10b-hexahydro-phenanthridin-2-ol citrate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol citrate;

(2R,4aR,10bR)-6-(4,6-Dimethoxy-pyridin-3-yl)-9-ethoxy-8-methoxy-1,2,3,4,4a, 10b-hexahydro-phenanthridin-2-ol citrate;

(2R,4aR,10bR)-6-(2-Dimethylamino-pyrimidin-5-yl)-9-ethoxy-8-methoxy-1,2,3,4,4a, 10b-hexahydro-phenanthridin-2-ol citrate;

(2R,4aR,10bR)-6-(5,6-Dimethoxy-pyridin-3-yl)-9-ethoxy-8-methoxy-1,2,3,4,4a, 10b-hexahydro-phenanthridin-2-ol citrate;

(2R,4aR,10bR)-9-Ethoxy-8-methoxy-6-(2-methylsulfanyl-pyrimidin-5-yl)-1,2,3,4,4a, 10b-hexahydro-phenanthridin-2-ol citrate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one citrate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one citrate;

(2R,4aR,10bR)-6-(2,6-Dimethoxy-pyridin-3-yl)-9-ethoxy-8-methoxy-1,2,3,4,4a, 10b-hexahydro-phenanthridin-2-ol L-tartrate;

(2R,4aR,10bR)-9-Ethoxy-8-methoxy-6-pyrimidin-5-yl-1,2,3,4,4a, 10b-hexahydro-phenanthridin-2-ol L-tartrate, m.p.: 166° C. (from acetone/isopropanol);

(2R,4aR,10bR)-9-Ethoxy-8-methoxy-6-(6-pyrazol-1-yl-pyridin-3-yl)-1,2,3,4,4a, 10b-hexahydro-phenanthridin-2-ol L-tartrate, m.p.: 177° C. (from acetone/isopropanol);

(2R,4aR,10bR)-9-Ethoxy-8-methoxy-6-(2-methoxy-pyrimidin-5-yl)-1,2,3,4,4a, 10b-hexahydro-phenanthridin-2-ol L-tartrate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol L-tartrate;

(2R,4aR,10bR)-9-Ethoxy-8-methoxy-6-pyrazin-2-yl-1,2,3,4,4a, 10b-hexahydro-phenanthridin-2-ol L-tartrate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol L-tartrate, m.p.: 203° C. (from acetone/isopropanol);

(2R,4aR,10bR)-9-Ethoxy-8-methoxy-6-(6-methoxy-pyridin-3-yl)-1,2,3,4,4a, 10b-hexahydro-phenanthridin-2-ol L-tartrate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol L-tartrate, m.p.: 249° C. (from acetone/isopropanol);

(2R,4aR,10bR)-6-(4,6-Dimethoxy-pyridin-3-yl)-9-ethoxy-8-methoxy-1,2,3,4,4a, 10b-hexahydro-phenanthridin-2-ol L-tartrate, m.p.: 190° C. (from acetone/isopropanol);

(2R,4aR,10bR)-6-(2-Dimethylamino-pyrimidin-5-yl)-9-ethoxy-8-methoxy-1,2,3,4,4a, 10b-hexahydro-phenanthridin-2-ol L-tartrate, m.p.: 206° C. (from acetone/isopropanol/dichloromethane);

(2R,4aR,10bR)-6-(5,6-Dimethoxy-pyridin-3-yl)-9-ethoxy-8-methoxy-1,2,3,4,4a, 10b-hexahydro-phenanthridin-2-ol L-tartrate;

(2R,4aR,10bR)-9-Ethoxy-8-methoxy-6-(2-methylsulfanyl-pyrimidin-5-yl)-1,2,3,4,4a, 10b-hexahydro-phenanthridin-2-ol L-tartrate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one L-tartrate, m.p.: 205° C. (from acetone/isopropanol);

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one L-tartrate;

(2R,4aR,10bR)-6-(2,6-Dimethoxy-pyridin-3-yl)-9-ethoxy-8-methoxy-1,2,3,4,4a, 10b-hexahydro-phenanthridin-2-ol D-tartrate, m.p.: fnd.: decomposition starting at 107° C. (from acetone);

(2R,4aR,10bR)-9-Ethoxy-8-methoxy-6-(2-methoxy-pyrimidin-5-yl)-1,2,3,4,4a, 10b-hexahydro-phenanthridin-2-ol D-tartrate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol D-tartrate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol D-tartrate;

(2R,4aR,10bR)-9-Ethoxy-8-methoxy-6-pyrazin-2-yl-1,2,3,4,4a, 10b-hexahydro-phenanthridin-2-ol D-tartrate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol D-tartrate;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol D-tartrate;

(2R,4aR,10bR)-6-(4,6-Dimethoxy-pyridin-3-yl)-9-ethoxy-8-methoxy-1,2,3,4,4a, 10b-hexahydro-phenanthridin-2-ol D-tartrate;

(2R,4aR,10bR)-6-(2-Dimethylamino-pyrimidin-5-yl)-9-ethoxy-8-methoxy-1,2,3,4,4a, 10b-hexahydro-phenanthridin-2-ol D-tartrate;

(2R,4aR,10bR)-6-(5,6-Dimethoxy-pyridin-3-yl)-9-ethoxy-8-methoxy-1,2,3,4,4a, 10b-hexahydro-phenanthridin-2-ol D-tartrate;

(2R,4aR,10bR)-9-Ethoxy-8-methoxy-6-(2-methylsulfanyl-pyrimidin-5-yl)-1,2,3,4,4a, 10b-hexahydro-phenanthridin-2-ol D-tartrate;

(2R,4aR,10bR)-9-Ethoxy-8-methoxy-6-(6-methoxy-pyridin-3-yl)-1,2,3,4,4a, 10b-hexahydro-phenanthridin-2-ol D-tartrate;

5-((2R,4aR,10bR)-9-Ethoxy-2-hydroxy-8-methoxy-1,2,3,4, 4a, 10b-hexahydro-phenanthridin-6-yl)-1-methyl-1H-pyridin-2-one D-tartrate;

5-((2R,4aR,10bR)-9-Ethoxy-2-hydroxy-8-methoxy-1,2,3,4, 4a, 10b-hexahydro-phenanthridin-6-yl)-1-methyl-1H-pyrimidin-2-one D-tartrate;

(2R,4aR,10bR)-6-(2,6-Dimethoxy-pyridin-3-yl)-9-ethoxy-8-methoxy-1,2,3,4,4a, 10b-hexahydro-phenanthridin-2-ol meso-tartrate;

(2R,4aR,10bR)-9-Ethoxy-8-methoxy-6-pyrimidin-5-yl-1,2, 3,4,4a, 10b-hexahydro-phenanthridin-2-ol meso-tartrate;

(2R,4aR,10bR)-9-Ethoxy-8-methoxy-6-(2-methoxy-pyrimidin-5-yl)-1,2,3,4,4a, 10b-hexahydro-phenanthridin-2-ol meso-tartrate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol meso-tartrate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol meso-tartrate;

(2R,4aR,10bR)-9-Ethoxy-8-methoxy-6-pyrazin-2-yl-1,2,3, 4,4a, 10b-hexahydro-phenanthridin-2-ol meso-tartrate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol meso-tartrate;

(2R,4aR,10bR)-6-(2-Dimethylamino-4-methoxy-pyrmidin-5-yl)-9-ethoxy-8-methoxy-1,2,3,4,4a, 10b-hexahydro-phenanthridin-2-ol meso-tartrate;

(2R,4aR,10bR)-6-(4,6-Dimethoxy-pyridin-3-yl)-9-ethoxy-8-methoxy-1,2,3,4,4a, 10b-hexahydro-phenanthridin-2-ol meso-tartrate;

(2R,4aR,10bR)-6-(2-Dimethylamino-pyrimidin-5-yl)-9-ethoxy-8-methoxy-1,2,3,4,4a, 10b-hexahydro-phenanthridin-2-ol meso-tartrate;

(2R,4aR,10bR)-6-(5,6-Dimethoxy-pyridin-3-yl)-9-ethoxy-8-methoxy-1,2,3,4,4a, 10b-hexahydro-phenanthridin-2-ol meso-tartrate;

(2R,4aR,10bR)-9-Ethoxy-8-methoxy-6-(2-methylsulfanyl-pyrimidin-5-yl)-1,2,3,4,4a, 10b-hexahydro-phenanthridin-2-ol meso-tartrate;

(2R,4aR,10bR)-9-Ethoxy-8-methoxy-6-(6-methoxy-pyridin-3-yl)-1,2,3,4,4a, 10b-hexahydro-phenanthridin-2-ol meso-tartrate;

5-((2R,4aR,10bR)-9-Ethoxy-2-hydroxy-8-methoxy-1,2,3,4, 4a, 10b-hexahydro-phenanthridin-6-yl)-1-methyl-1H-pyridin-2-one meso-tartrate;

5-((2R,4aR,10bR)-9-Ethoxy-2-hydroxy-8-methoxy-1,2,3,4, 4a, 10b-hexahydro-phenanthridin-6-yl)-1-methyl-1H-pyrimidin-2-one meso-tartrate;

(2R,4aR,10bR)-6-(2,6-Dimethoxy-pyridin-3-yl)-9-ethoxy-8-methoxy-1,2,3,4,4a, 10b-hexahydro-phenanthridin-2-ol D-malate;

(2R,4aR,10bR)-9-Ethoxy-8-methoxy-6-(6-pyrazol-1-yl-pyridin-3-yl)-1,2,3,4,4a, 10b-hexahydro-phenanthridin-2-ol D-malate;

(2R,4aR,10bR)-9-Ethoxy-8-methoxy-6-(2-methoxy-pyrimidin-5-yl)-1,2,3,4,4a, 10b-hexahydro-phenanthridin-2-ol D-malate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol D-malate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol D-malate;

(2R,4aR,10bR)-6-(2-Dimethylamino-4-methoxy-pyrimidin-5-y)-9-ethoxy-8-methoxy-1,2,3,4,4a,10b-hexahydro-phenanthridin-2-ol D-malate;

(2R,4aR,10bR)-6-(4,6-Dimethoxy-pyridin-3-yl)-9-ethoxy-8-methoxy-1,2,3,4,4a, 10b-hexahydro-phenanthridin-2-ol D-malate;

(2R,4aR,10bR)-6-(5,6-Dimethoxy-pyridin-3-yl)-9-ethoxy-8-methoxy-1,2,3,4,4a, 10b-hexahydro-phenanthridin-2-ol D-malate;

(2R,4aR,10bR)-9-Ethoxy-8-methoxy-6-(2-methylsulfanyl-pyrimidin-5yl)-1,2,3,4,4a, 10b-hexahydro-phenanthridin-2-ol D-malate;

(2R,4aR,10bR)-9-Ethoxy-8-methoxy-6-(6-methoxy-pyridin-3-yl)-1,2,3,4,4a, 10b-hexahydro-phenanthridin-2-ol D-malate;

5-((2R,4aR,10bR)-9-Ethoxy-2-hydroxy-8-methoxy-1,2,3,4, 4a, 10b-hexahydro-phenanthridin-6-yl)-1-methyl-1H-pyridin-2-one D-malate;

5-((2R,4aR,10bR)-9-Ethoxy-2-hydroxy-8-methoxy-1,2,3,4, 4a, 10b-hexahydro-phenanthridin-6-yl)-1-methyl-1H-pyrimidin-2-one D-malate;

(2R,4aR,10bR)-6-(2,6-Dimethoxy-pyridin-3-yl)-9-ethoxy-8-methoxy-1,2,3,4,4a, 10b-hexahydro-phenanthridin-2-ol L-malate;

(2R,4aR,10bR)-9-Ethoxy-8-methoxy-6-pyrimidin-5-yl-1,2, 3,4,4a, 10b-hexahydro-phenanthridin-2-ol L-malate;

(2R,4aR,10bR)-9-Ethoxy-8-methoxy-6-(2-methoxy-pyrimidin-5-yl)-1,2,3,4,4a, 10-hexahydro-phenanthridin-2-ol L-malate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol L-malate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol L-malate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol L-malate;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol L-malate;

(2R,4aR,10bR)-6-(4,6-Dimethoxy-pyridin-3-yl)-9-ethoxy-8-methoxy-1,2,3,4,4a, 10b-hexahydro-phenanthridin-2-ol L-malate;

(2R,4aR,10bR)-6-(5,6-Dimethoxy-pyridin-3-yl)-9-ethoxy-8-methoxy-1,2,3,4,4a, 10b-hexahydro-phenanthridin-2-ol L-malate;

(2R,4aR,10bR)-9-Ethoxy-8-methoxy-6-(2-methylsulfanyl-pyrimidin-5-yl)-1,2,3,4,4a, 10b-hexahydro-phenanthridin-2-ol L-malate;

(2R,4aR,10bR)-9-Ethoxy-8-methoxy-6-(6-methoxy-pyridin-3-yl)-1,2,3,4,4a, 10b-hexahydro-phenanthridin-2-ol L-malate;

5-((2R,4aR,10bR)-9-Ethoxy-2-hydroxy-8-methoxy-1,2,3,4, 4a, 10b-hexahydro-phenanthridin-6-yl)-1-methyl-1H-pyridin-2-one L-malate;

5-((2R,4aR,10bR)-9-Ethoxy-2-hydroxy-8-methoxy-1,2,3,4, 4a,10b-hexahydro-phenanthridin-6-yl)-1-methyl-1H-pyrmidin-2-one L-malate;

(2R,4aR,10bR)-6-(2,6-Dimethoxy-pyridin-3-yl)-9-ethoxy-8-methoxy-1,2,3,4,4a,10b-hexahydro-phenanthridin-2-ol fumarate, m.p.: fnd.: decompositon starting at 172° C. (from acetone);

(2R,4aR,10bR)-9-Ethoxy-8-methoxy-6-pyrimidin-5-yl-1,2, 3,4,4a,10b-hexahydro-phenanthridin-2-ol fumarate;

(2R,4aR,10bR)-9-Ethoxy-8-methoxy-6-(6-pyrazol-1-yl-pyridin-3-yl)-1,2,3,4,4a, 10b-hexahydro-phenanthridin-2-ol fumarate, m.p.: 170° C. (from acetone/isopropanol);

(2R,4aR,10bR)-9-Ethoxy-8-methoxy-6-(2-methoxy-pyrimidin-5-yl)-1,2,3,4,4a, 10b-hexahydro-phenanthridin-2-ol fumarate, m.p.: 124° C. (from acetone/isopropanol);

(2R,4aR,10bR)-6-(2,4-Dimethoxy-pyrimidin-5-yl)-9-ethoxy-8-methoxy-1,2,3,4,4a, 10b-hexahydro-phenanthridin-2-ol fumarate;

(2R,4aR,10bR)-9-Ethoxy-6-(6-imidazol-1-yl-pyridin-3-yl)-8-methoxy-1,2,3,4,4a, 10b-hexahydro-phenanthridin-2-ol fumarate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol fumarate, m.p.: 202° C. (from acetone/isopropanol);

(2R,4aR,10bR)-9-Ethoxy-8-methoxy-6-(6-methoxy-pyridin-3-yl)-1,2,3,4,4a, 10b-hexahydro-phenanthrdin-2-ol fumarate, m.p.: 173° C. (from acetone/isopropanol);

(2R,4aR,10bR)-6-(2-Dimethylamino-4-methoxy-pyrimidin-5-yl)-9-ethoxy-8-methoxy-1,2,3,4,4a,10b-hexahydro-phenanthrdin-2-ol fumarate, m.p. 123° C. (from acetone/isopropanol);

(2R,4aR,10bR)-6-(4,6-Dimethoxy-pyridin-3-yl)-9-ethoxy-8-methoxy-1,2,3,4,4a, 10b-hexahydro-phenanthridin-2-ol fumarate, m.p.: 194° C. (from acetone/isopropanol);

(2R,4aR,10bR)-6-(2-Dimethylamino-pyrimidin-5-yl)-9-ethoxy-8-methoxy-1,2,3,4,4a, 10b-hexahydro-phenanthridin-2-ol fumarate, m.p.: 210° C. (from acetone/isopropanol/dichloromethane);

(2R,4aR,10bR)-6-(5,6-Dimethoxy-pyridin-3-yl)-9-ethoxy-8-methoxy-1,2,3,4,4a, 10b-hexahydro-phenanthridin-2-ol fumarate;

(2R,4aR,10bR)-9-Ethoxy-8-methoxy-6-(2-methylsulfanyl-pyrimidin-5-yl)-1,2,3,4,4a, 10b-hexahydro-phenanthridin-2-ol fumarate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one fumarate, m.p.: 156° C. (from acetone/isopropanol);

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one fumarate;

(2R,4aR,10bR)-6-(2,6-Dimethoxy-pyridin-3-yl)-9-ethoxy-8-methoxy-1,2,3,4,4a, 10b-hexahydro-phenanthridin-2-ol maleinate;

(2R,4aR,10bR)-9-Ethoxy-8-methoxy-6-pyrimidin-5-yl-1,2,3,4,4a, 10b-hexahydro-phenanthridin-2-ol maleinate;

(2R,4aR,10bR)-9-Ethoxy-8-methoxy-6-(2-methoxy-pyrimidin-5-yl)-1,2,3,4,4a, 10b-hexahydro-phenanthridin-2-ol maleinate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol maleinate;

(2R,4aR,10bR)-9-Ethoxy-8-methoxy-6-pyrazin-2-yl-1,2,3,4,4a, 10b-hexahydro-phenanthridin-2-ol maleinate;

(2R,4aR,10bR)-6-(3,6-Dimethoxy-pyridazin-4-yl)-9-ethoxy-8-methoxy-1,2,3,4,4a, 10b-hexahydro-phenanthridin-2-ol maleinate;

(2R,4aR,10bR)-9-Ethoxy-8-methoxy-6-(6-methoxy-pyridin-3-yl)-1,2,3,4,4a, 10b-hexahydro-phenanthridin-2-ol maleinate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol maleinate;

(2R,4aR,10bR)-6-(4,6-Dimethoxy-pyridin-3-yl)-9-ethoxy-8-methoxy-1,2,3,4,4a, 10b-hexahydro-phenanthridin-2-ol maleinate;

(2R,4aR,10bR)-6-(2-Dimethylamino-pyrimidin-5-yl)-9-ethoxy-8-methoxy-1,2,3,4,4a, 10b-hexahydro-phenanthridin-2-ol maleinate;

(2R,4aR,10bR)-6-(5,6-Dimethoxy-pyridin-3-yl)-9-ethoxy-8-methoxy-1,2,3,4,4a, 10b-hexahydro-phenanthridin-2-ol maleinate;

(2R,4aR,10bR)-9-Ethoxy-8-methoxy-6-(2-methylsulfanyl-pyrimidin-5-yl)-1,2,3,4,4a, 10b-hexahydro-phenanthridin-2-ol maleinate;

5-((2R,4aR,10bR)-9-Ethoxy-2-hydroxy-8-methoxy-1,2,3,4,4a, 10b-hexahydro-phenanthridin-6-yl)-1-methyl-1H-pyridin-2-one maleinate;

5-((2R,4aR,10bR)-9-Ethoxy-2-hydroxy-8-methoxy-1,2,3,4,4a, 10b-hexahydro-phenanthridin-6-yl)-1-methyl-1H-pyrimidin-2-one maleinate;

(2R,4aR,10bR)-6-(2,6-Dimethoxy-pyridin-3-yl)-9-ethoxy-8-methoxy-1,2,3,4,4a, 10b-hexahydro-phenanthridin-2-ol 2-oxoglutarate, m.p.: fnd.: decomposition starting at 110° C. (from acetone);

(2R,4aR,10bR)-9-Ethoxy-8-methoxy-6-pyrimidin-5-yl-1,2,3,4,4a,10b-hexahydro-phenanthridin-2-ol 2-oxoglutarate;

(2R,4aR,10bR)-9-Ethoxy-8-methoxy-6-(6-pyrazol-1-yl-pyridin-3-yl)-1,2,3,4,4a, 10b-hexahydro-phenanthridin-2-ol 2-oxoglutarate, m.p.: 218° C. (from acetone);

(2R,4aR,10bR)-9-Ethoxy-8-methoxy-6-(2-methoxy-pyrimidin-5-yl)-1,2,3,4,4a, 10b-hexahydro-phenanthridin-2-ol 2-oxoglutarate;

(2R,4aR,10bR)-6-(2,4-Dimethoxy-pyrimidin-5-yl)-9-ethoxy-8-methoxy-1,2,3,4,4a, 10b-hexahydro-phenanthridin-2-ol 2-oxoglutarate, m.p.: 171° C. (from acetone);

(2R,4aR,10bR)-9-Ethoxy-6-(6-imidazol-1-yl-pyridin-3-yl)-8-methoxy-1,2,3,4,4a, 10b-hexahydro-phenanthridin-2-ol 2-oxoglutarate;

(2R,4aR,10bR)-9-Ethoxy-8-methoxy-6-pyrazin-2-yl-1,2,3,4,4a, 10b-hexahydro-phenanthridin-2-ol 2-oxoglutarate;

(2R,4aR, 10bR)-6-(3,6-Dimethoxy-pyridazin-4-yl)-9-ethoxy-8-methoxy-1,2,3,4,4a, 10b-hexahydro-phenanthridin-2-ol 2-oxoglutarate, m.p.: 202° C. (from acetone);

(2R,4aR,10bR)-9-Ethoxy-8-methoxy-6-(6-methoxy-pyridin-3-yl)-1,2,3,4,4a, 10b-hexahydro-phenanthridin-2-ol 2-oxoglutarate;

(2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol 2-oxoglutarate, m.p.: 124° C. (from acetone);

(2R,4aR,10bR)-6-(4,6-Dimethoxy-pyridin-3-yl)-9-ethoxy-8-methoxy-1,2,3,4,4a, 10b-hexahydro-phenanthridin-2-of 2-oxoglutarate, m.p.: 143° C. (from acetone);

(2R,4aR,10bR)-6-(2-Dimethylamino-pyrimidin-5-yl)-9-ethoxy-8-methoxy-1,2,3,4,4a, 10b-hexahydro-phenanthridin-2-ol 2-oxoglutarate, m.p.: 112° C. (from acetone/dichloromethane);

(2R,4aR,10bR)-6-(5,6-Dimethoxy-pyridin-3-yl)-9-ethoxy-8-methoxy-1,2,3,4,4a, 10b-hexahydro-phenanthridin-2-ol 2-oxoglutarate;

(2R,4aR,10bR)-9-Ethoxy-8-methoxy-6-(2-methylsulfanyl-pyrimidin-5-yl)-1,2,3,4,4a, 10b-hexahydro-phenanthrdin-2-ol 2-oxoglutarate;

5-((2R,4aR,10bR)-9-Ethoxy-2-hydroxy-8-methoxy-1,2,3,4, 4a, 10b-hexahydro-phenanthridin-6-yl)-1-methyl-1H-pyridin-2-one 2-oxoglutarate, m.p.: 147° C. (from acetone);

5-((2R,4aR,10bR)-9-Ethoxy-2-hydroxy-8-methoxy-1,2,3,4, 4a, 10b-hexahydro-phenanthridin-6-yl)-1-methyl-1H-pyrimidin-2-one 2-oxoglutarate;

(2R,4aR,10bR)-6-(2,6-Dimethoxy-pyridin-3-yl)-9-ethoxy-8-methoxy-1,2,3,4,4a,10b-hexahydro-phenanthridin-2-ol edisilate;

(2R,4aR,10bR)-9-Ethoxy-8-methoxy-6-pyrmidin-5-yl-1,2,3,4,4a,10b-hexahydro-phenanthridin-2-ol edisilate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol edisilate;

(2R,4aR,10bR)-9-Ethoxy-8-methoxy-6-(2-methoxy-pyrimidin-5-yl)-1,2,3,4,4a,10b-hexahydro-phenanthridin-2-ol edisilate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol edisilate;

(2R,4aR,10bR)-9-Ethoxy-6-(6-imidazol-1-yl-pyridin-3-yl)-8-methoxy-1,2,3,4,4a,10b-hexahydro-phenanthridin-2-ol edisilate;

(2R,4aR,10bR)-9-Ethoxy-8-methoxy-6-pyrazin-2-yl-1,2,3,4,4a,10b-hexahydro-phenanthridin-2-ol edisilate;

(2R,4aR,10bR)-6-(3,6-Dimethoxy-pyridazin-4-yl)-9-ethoxy-8-methoxy-1,2,3,4,4a,10b-hexahydro-phenanthridin-2-ol edisilate;

(2R,4aR,10bR)-9-Ethoxy-8-methoxy-6-(6-methoxy-pyridin-3-yl)-1,2,3,4,4a,10b-hexahydro-phenanthridin-2-ol edisilate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol edisilate;

(2R,4aR,10bR)-6-(4,6-Dimethoxy-pyridin-3-yl)-9-ethoxy-8-methoxy-1,2,3,4,4a,10b-hexahydro-phenanthridin-2-ol edisilate;

(2R,4aR,10bR)-6-(2-Dimethylamino-pyrimidin-5-yl)-9-ethoxy-8-methoxy-1,2,3,4,4a,10b-hexahydro-phenanthridin-2-ol edisilate;

(2R,4aR,10bR)-6-(5,6-Dimethoxy-pyridin-3-yl)-9-ethoxy-8-methoxy-1,2,3,4,4a,10b-hexahydro-phenanthridin-2-ol edisilate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol edisilate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one edisilate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one edisilate;

(2R,4aR,10bR)-6-(2,6-Dimethoxy-pyridin-3-yl)-9-ethoxy-8-methoxy-1,2,3,4,4a,10b-hexahydro-phenanthridin-2-ol esilate;

(2R,4aR,10bR)-9-Ethoxy-8-methoxy-6-pyrimidin-5-yl-1,2,3,4,4a,10b-hexahydro-phenanthridin-2-ol esilate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol esilate;

(2R,4aR,10bR)-9-Ethoxy-8-methoxy-6-(2-methoxy-pyrimidin-5-yl)-1,2,3,4,4a,10b-hexahydro-phenanthridin-2-ol esilate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol esilate;

(2R,4aR,10bR)-9-Ethoxy-6-(6-imidazol-1-yl-pyridin-3-yl)-8-methoxy-1,2,3,4,4a,10b-hexahydro-phenanthridin-2-ol esilate;

(2R,4aR,10bR)-9-Ethoxy-8-methoxy-6-pyrazin-2-yl-1,2,3,4,4a,10b-hexahydro-phenanthridin-2-ol esilate;

(2R,4aR,10bR)-6-(3,6-Dimethoxy-pyridazin-4-yl)-9-ethoxy-8-methoxy-1,2,3,4,4a,10b-hexahydro-phenanthridin-2-ol esilate;

(2R,4aR,10bR)-9-Ethoxy-8-methoxy-6-(6-methoxy-pyridin-3-yl)-1,2,3,4,4a,10b-hexahydro-phenanthridin-2-ol esilate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol esilate;

(2R,4aR,10bR)-6-(4,6-Dimethoxy-pyridin-3-yl)-9-ethoxy-8-methoxy-1,2,3,4,4a,10b-hexahydro-phenanthridin-2-ol esilate;

(2R,4aR,10bR)-6-(2-Dimethylamino-pyrimidin-5-yl)-9-ethoxy-8-methoxy-1,2,3,4,4a,10b-hexahydro-phenanthridin-2-ol esilate;

(2R,4aR,10bR)-6-(5,6-Dimethoxy-pyridin-3-yl)-9-ethoxy-8-methoxy-1,2,3,4,4a,10b-hexahydro-phenanthridin-2-ol esilate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol esilate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one esilate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one esilate;

(2R,4aR,10bR)-6-(2,6-Dimethoxy-pyridin-3-yl)-9-ethoxy-8-methoxy-1,2,3,4,4a,10b-hexahydro-phenanthridin-2-ol hydrobromide;

(2R,4aR,10bR)-9-Ethoxy-8-methoxy-6-pyrimidin-5-yl-1,2,3,4,4a,10b-hexahydro-phenanthridin-2-ol hydrobromide;

(2R,4aR,10bR)-9-Ethoxy-8-methoxy-6-(6-pyrazol-1-yl-pyridin-3-yl)-1,2,3,4,4a,10b-hexahydro-phenanthridin-2-ol hydrobromide;

(2R,4aR,10bR)-9-Ethoxy-8-methoxy-6-(2-methoxy-pyrimidin-5-yl)-1,2,3,4,4a,10b-hexahydro-phenanthridin-2-ol hydrobromide;

(2R,4aR,10bR)-6-(2,4-Dimethoxy-pyrimidin-5-yl)-9-ethoxy-8-methoxy-1,2,3,4,4a,10b-hexahydro-phenanthridin-2-ol hydrobromide;

(2R,4aR,10bR)-9-Ethoxy-6-(6-imidazol-1-yl-pyridin-3-yl)-8-methoxy-1,2,3,4,4a,10b-hexahydro-phenanthridin-2-ol hydrobromide;

(2R,4aR,10bR)-9-Ethoxy-8-methoxy-6-pyrazin-2-yl-1,2,3,4,4a,10b-hexahydro-phenanthridin-2-ol hydrobromide;

(2R,4aR,10bR)-6-(3,6-Dimethoxy-pydazin-4-yl)-9-ethoxy-8-methoxy-1,2,3,4,4a,10b-hexahydro-phenanthridin-2-ol hydrobromide;

(2R,4aR,10bR)-9-Ethoxy-8-methoxy-6-(6-methoxy-pyridin-3-yl)-1,2,3,4,4a,10b-hexahydro-phenanthridin-2-ol hydrobromide;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol hydrobromide;

(2R,4aR,10bR)-6-(4,6-Dimethoxy-pyridin-3-yl)-9-ethoxy-8-methoxy-1,2,3,4,4a,10b-hexahydro-phenanthridin-2-ol hydrobromide;

(2R,4aR,10bR)-6-(2-Dimethylamino-pyrimidin-5-yl)-9-ethoxy-8-methoxy-1,2,3,4,4a,10b-hexahydro-phenanthridin-2-ol hydrobromide;

(2R,4aR,10bR)-6-(5,6-Dimethoxy-pyridin-3-yl)-9-ethoxy-8-methoxy-1,2,3,4,4a,10b-hexahydro-phenanthridin-2-ol hydrobromide;

(2R,4aR,10bR)-9-Ethoxy-8-methoxy-6-(2-methylsulfanyl-pyrimidin-5-yl)-1,2,3,4,4a,10b-hexahydro-phenanthridin-2-ol hydrobromide;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one hydrobromide;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one hydrobromide;

(2R,4aR,10bR)-6-(2,6-Dimethoxy-pyridin-3-yl)-9-ethoxy-8-methoxy-1,2,3,4,4a,10b-hexahydro-phenanthrdin-2-ol tosylate;

(2R,4aR,10bR)-9-Ethoxy-8-methoxy-6-pyrimidin-5-yl-1,2,3,4,4a,10b-hexahydro-phenanthridin-2-ol tosylate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol tosylate;

(2R,4aR,10bR)-9-Ethoxy-8-methoxy-6-(2-methoxy-pyrimidin-5-yl)-1,2,3,4,4a,10b-hexahydro-phenanthridin-2-ol tosylate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol tosylate;

(2R,4aR,10bR)-9-Ethoxy-6-(6-imidazol-1-yl-pyridin-3-yl)-8-methoxy-1,2,3,4,4a,10b-hexahydro-phenanthridin-2-ol tosylate;

(2R,4aR,10bR)-9-Ethoxy-8-methoxy-6-pyrazin-2-yl-1,2,3,4,4a,10b-hexahydro-phenanthridin-2-ol tosylate;

(2R,4aR,10bR)-6-(3,6-Dimethoxy-pyridazin-4-yl)-9-ethoxy-8-methoxy-1,2,3,4,4a,10b-hexahydro-phenanthridin-2-ol tosylate;

(2R,4aR,10bR)-9-Ethoxy-8-methoxy-6-(6-methoxy-pyridin-3-yl)-1,2,3,4,4a,10b-hexahydro-phenanthridin-2-ol tosylate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol tosylate;

(2R,4aR,10bR)-6-(4,6-Dimethoxy-pyridin-3-yl)-9-ethoxy-8-methoxy-1,2,3,4,4a,10b-hexahydro-phenanthridin-2-ol tosylate;

(2R,4aR,10bR)-6-(2-Dimethylamino-pyrimidin-5-yl)-9-ethoxy-8-methoxy-1,2,3,4,4a,10b-hexahydro-phenanthridin-2-ol tosylate;

(2R,4aR,10bR)-6-(5,6-Dimethoxy-pyridin-3-yl)-9-ethoxy-8-methoxy-1,2,3,4,4a,10b-hexahydro-phenanthridin-2-ol tosylate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol tosylate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one tosylate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one tosylate;

(2R,4aR,10bR)-6-(2,6-Dimethoxy-pyridin-3-yl)-9-ethoxy-8-methoxy-1,2,3,4,4a,10b-hexahydro-phenanthridin-2-ol oxalate;

(2R,4aR,10bR)-9-Ethoxy-8-methoxy-6-pyrimidin-5-yl-1,2,3,4,4a,10b-hexahydro-phenanthrdin-2-ol oxalate, m.p.: 126° C. (from acetone);

(2R,4aR,10bR)-9-Ethoxy-8-methoxy-6-(2-methoxy-pyrimidin-5-yl)-1,2,3,4,4a,10b-hexahydro-phenanthridin-2-ol oxalate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol oxalate;

(2R,4aR,10bR)-9-Ethoxy-6-(6-imidazol-1-yl-pyridin-3-yl)-8-methoxy-1,2,3,4,4a,10b-hexahydro-phenanthridin-2-ol oxalate;

(2R,4aR,10bR)-6-(3,6-Dimethoxy-pyridazin-4-yl)-9-ethoxy-8-methoxy-1,2,3,4,4a,10b-hexahydro-phenanthridin-2-ol oxalate;

(2R,4aR,10bR)-6-(4,6-Dimethoxy-pyridin-3-yl)-9-ethoxy-8-methoxy-1,2,3,4,4a,10b-hexahydro-phenanthridin-2-ol oxalate, m.p.: 181° C. (from acetone);

(2R,4aR,10bR)-6-(2-Dimethylamino-pyrimidin-5-yl)-9-ethoxy-8-methoxy-1,2,3,4,4a,10b-hexahydro-phenanthridin-2-ol oxalate;

(2R,4aR,10bR)-6-(5,6-Dimethoxy-pyridin-3-yl)-9-ethoxy-8-methoxy-1,2,3,4,4a,10b-hexahydro-phenanthridin-2-ol oxalate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol oxalate;

(2R,4aR,10bR)-9-Ethoxy-8-methoxy-6-(6-methoxy-pyridin-3-yl)-1,2,3,4,4a,10b-hexahydro-phenanthridin-2-ol oxalate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one oxalate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one oxalate;

(2R,4aR,10bR)-6-(2,6-Dimethoxy-pyridin-3-yl)-9-ethoxy-8-methoxy-1,2,3,4,4a,10b-hexahydro-phenanthridin-2-ol D-gluconate;

(2R,4aR,10bR)-9-Ethoxy-8-methoxy-6-pyrimidin-5-yl-1,2,3,4,4a,10b-hexahydro-phenanthridin-2-ol D-gluconate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol D-gluconate;

(2R,4aR,10bR)-9-Ethoxy-8-methoxy-6-(2-methoxy-pyrimidin-5-yl)-1,2,3,4,4a,10b-hexahydro-phenanthridin-2-ol D-gluconate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol D-gluconate;

(2R,4aR,10bR)-9-Ethoxy-8-methoxy-6-pyrazin-2-yl-1,2,3,4,4a,10b-hexahydro-phenanthridin-2-ol D-gluconate;

(2R,4aR,10bR)-6-(3,6-Dimethoxy-pyridazin-4-yl)-9-ethoxy-8-methoxy-1,2,3,4,4a,10b-hexahydro-phenanthridin-2-ol D-gluconate;

(2R,4aR,10bR)-9-Ethoxy-8-methoxy-6-(6-methoxy-pyridin-3-yl)-1,2,3,4,4a,10b-hexahydro-phenanthrdin-2-ol D-gluconate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-gluconate;

(2R,4aR,10bR)-6-(4,6-Dimethoxy-pyridin-3-yl)-9-ethoxy-8-methoxy-1,2,3,4,4a,10b-hexahydro-phenanthridin-2-ol D-gluconate;

(2R,4aR,10bR)-6-(5,6-Dimethoxy-pyridin-3-yl)-9-ethoxy-8-methoxy-1,2,3,4,4a,10b-hexahydro-phenanthridin-2-ol D-gluconate;

(2R,4aR,10bR)-9-Ethoxy-8-methoxy-6-(2-methylsulfanyl-pyrimidin-5-yl)-1,2,3,4,4a,10b-hexahydro-phenanthridin-2-ol D-gluconate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one D-gluconate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one D-gluconate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol oxalate, m. p.: 212.0° C. (from acetone); and (2R,4aR,10bR)-9-Ethoxy-8-methoxy-6-pyrazin-2-yl-1,2,3, 4,4a, 10b-hexahydro-phenanthridin-2-ol oxalate, m. p.: 170.6° C. (from acetone).

Optionally the abovementioned salts can be converted in a suitable solvent with the aid of a suitable base into the free compounds, which can be isolated in a manner known per se.

Free Bases 1. (2RS,4aR S,10bRS)-6-(2,6-Dimethoxy-pyridin-3-yl)-9-ethoxy-8-methoxy-1,2,3,4,4a,10b-hexahydro-phenanthridin-2-ol 423 mg of acetic acid (2RS,4aR S,10bRS)-6-(2,6-dimethoxy-pyridin-3-yl)-9-ethoxy-8-methoxy-1,2,3,4,4a, 10b-hexahydro-phenanthridin-2-yl ester (compound 18) dissolved in 1 ml of dichloro-methane and 9 ml of methanol are added to 152 mg of cesium carbonate and the solution stirred for 19 h. The reaction mixture is adsorbed to silica gel and purified by flash chromatography to give 229 mg of the title compound as a colourless foam.

EF: $C_{23}H_{28}N_2O_5$; MW: calc.: 412.49. MS: fnd.: 413.3 (MH$^+$).

Starting from the appropriate ester compounds, which are mentioned or described explicitly below (compound 19 to 32) the following compounds are obtained according to the procedure as in compound 1 or analogously or similarly thereto.

2. (2R,4aR,10bR)-9-Ethoxy-8-methoxy-6-pyrimidin-5-yl-1, 2,3,4,4a, 10b-hexahydro-phenanthridin-2-ol Starting from compound 19 the title compound is obtained in an analogous manner as described for compound 1.

EF: $C_{20}H_{23}N_3O_3$; MW: calc.: 353,42. MS: fnd.: 354,3.

3. (2R,4aR,10bR)-9-Ethoxy-8-methoxy-6-(6-pyrazol-1-yl-pyridin-3-yl)-1,2,3,4,4a, 10b-hexahydro-phenanthridin-2-ol Starting from compound 20 the title compound is obtained in an analogous manner as described for compound 1.

EF: $C_{24}H_{26}N_4O_3$; MW: calc.: 418,5. MS: fnd.: 419,4. $[\alpha]^{20}_D=-84°$ 4. (2R,4aR,10bR)-9-Ethoxy-8-methoxy-6-(2-methoxy-pyrimidin-5-yl)-1,2,3,4,4a, 10b-hexahydro-phenanthridin-2-ol Starting from compound 21 the title compound is obtained in an analogous manner as described for compound 1.

EF: $C_{21}H_{25}N_3O_4$; MW: calc.: 383,45. MS: fnd.: 384,3.

5. (2R,4aR,10bR)-6-(2,4-Dimethoxy-pyrimidin-5-yl)-9-ethoxy-8-methoxy-1,2,3,4,4a, 10b-hexahydro-phenanthridin-2-ol Starting from compound 22 the title compound is obtained in an analogous manner as described for compound 1.

EF: $C_{22}H_{27}N_3O_5$; MW: calc.: 413,48. MS: fnd.: 414,3.

6. (2R,4aR,10bR)-9-Ethoxy-6-(6-imidazol-1-yl-pyridin-3-yl)-8-methoxy-1,2,3,4,4a, 10b-hexahydro-phenanthridin-2-ol Starting from compound 23 the title compound is obtained in an analogous manner as described for compound 1.

EF: $C_{24}H_{26}N_4O_3$; MW: calc.: 418,5. MS: fnd.: 419,3.

7. (2R,4aR,10bR)-9-Ethoxy-8-methoxy-6-pyrazin-2-yl-1,2, 3,4,4a, 10b-hexahydro-phenanthridin-2-ol Starting from compound 24 the title compound is obtained in an analogous manner as described for compound 1.

EF: $C_{20}H_{23}N_3O_3$; MW: calc.: 353,42. MS: fnd.: 354,3.

8. (2R,4aR,10bR)-6-(2,6-Dimethoxy-pyridin-3-yl)-9-ethoxy-8-methoxy-1,2,3,4,4a, 10b-hexahydro-phenanthridin-2-ol Starting from compound 25 the title compound is obtained in an analogous manner as described for compound 1.

Alternatively, the title compound can be obtained by chromatographical separation of the corresponding racemate (compound 1) using a column as described below at the end of the chapter.

EF: $C_{23}H_{28}N_2O_5$; MW: calc.: 412,49. MS: fnd.: 413,3.

9. 5-((2R,4aR,10bR)-9-Ethoxy-2-hydroxy-8-methoxy-1,2,3, 4,4a, 10b-hexahydro-phenanthridin-6-yl)-1-methyl-1H-pyridin-2-one Starting from compound 26 the title compound is obtained in an analogous manner as described for compound 1.

$C_{22}H_{26}N_2O_4$

Calc.: 382.46. MS: Found (MH$^+$): 383.2.

10. (2R,4aR,10bR)-9-Ethoxy-8-methoxy-6-(6-methoxy-pyridin-3-yl)-1,2,3,4,4a, 10b-hexahydro-phenanthridin-2-ol Starting from compound 27 the title compound is obtained in an analogous manner as described for compound 1.

$C_{22}H_{26}N_2O_4$

Calc.: 382.46. MS: Found (MH$^+$): 383.3.

11. (2R,4aR,10bR)-6-(2-Dimethylamino-4-methoxy-pyrimidin-5-yl)-9-ethoxy-8-methoxy-1,2,3,4,4a, 10b-hexahydro-phenanthridin-2-ol Starting from compound 28 the title compound is obtained in an analogous manner as described for compound 1.

$C_{23}H_{30}N_4O_4$

Calc.: 426.52. MS: Found (MH$^+$): 427.3.

12. (2R,4aR,10bR)-6-(4,6-Dimethoxy-pyridin-3-yl)-9-ethoxy-8-methoxy-1,2,3,4,4a, 10b-hexahydro-phenanthridin-2-ol Starting from compound 29 the title compound is obtained in an analogous manner as described for compound 1.

$C_{23}H_{28}N_2O_5$

Calc.: 412,49. MS: Found (MH$^+$): 413.3.

13. (2R,4aR,10bR)-6-(2-Dimethylamino-pyrimidin-5-yl)-9-ethoxy-8-methoxy-1,2,3,4,4a, 10b-hexahydro-phenanthridin-2-ol Starting from compound 30 the title compound is obtained in an analogous manner as described for compound 1.

$C_{22}H_{28}N_4O_3$

Calc.: 396,49. MS: Found (MH$^+$): 397.3.

14. 5-((2R,4aR,10bR)-9-Ethoxy-2-hydroxy-8-methoxy-1,2, 3,4,4a, 10b-hexahydro-phenanthridin-6-yl)-1-methyl-1H-pyrimidin-2-one Starting from compound 31 the title compound is obtained in an analogous manner as described for compound 1.

$C_{21}H_{25}N_3O_4$

Calc.: 383.45. MS: Found (MH$^+$): 384.2.

15. (2R,4aR,10bR)-6-(3,6-Dimethoxy-pyridazin-4-yl)-9-ethoxy-8-methoxy-1,2,3,4,4a, 10b-hexahydro-phenanthridin-2-ol Starting from compound 32 the title compound is obtained in an analogous manner as described for compound 1.

$C_{22}H_{27}N_3O_5$

Calc.: 413.48. MS: Found (MH$^+$): 414.3.

16. (2R,4aR,10bR)-6-(5,6-Dimethoxy-pyridin-3-yl)-9-ethoxy-8-ethoxy-1,2,3,4,4a, 10b-hexahydro-phenanthridin-2-ol Starting from compound 33 the title compound is obtained in an analogous manner as described for compound 1.

$C_{23}H_{28}N_2O_5$

Calc.: 412.49. MS: Found (MH$^+$): 413.3.

17. (2R,4aR,10bR)-9-Ethoxy-8-methoxy-6-(2-methylsulfanyl-pyrimidin-5-yl)-1,2,3,4,4a, 10b-hexahydro-phenanthridin-2-ol Starting from compound 34 the title compound is obtained in an analogous manner as described for compound 1.

$C_{21}H_{25}N_3O_3S$

Calc.: 399.52. MS: Found (MH$^+$): 400.3.

Chromatographical separation:

Alternatively to the above described synthesis procedures enantiomerically pure compounds can be obtained from the corresponding racemates by chromatographical separation, which can be afforded with one or more of the following chiral columns:

CHIRALPAK® AD-H 5 μm (250×20 mm), 25° C., heptane/2-propanol/diethylamine=90/10/0.1; 20 ml/min, detection at 340 nm;

CHIRALPAK® AD 20 μm (285×110 mm), 30° C., acetonitrile/isopropanol=95:5; 570 ml/min, detection at 250 nm or 280 nm;

CHIRALPAK® AD 20 μm (250×50 mm), ambient temperature, heptane/isopropanol=95:5, 120 ml/min, detection at 330 nm; or CHIRALPAK® 50801 20 μm (250×50 mm), 25° C., methanol, 120 ml/min, detection at 330 nm.

18. Acetic acid (2RS,4aRS,10bRS)-6-(2,6-dimethoxy-pyridin-3-yl)-9-ethoxy-8-methoxy-1,2,3,4,4a, 10b-hexahydro-phenanthridin-2-yl ester 1.67 g of phosphorus pentachloride are suspended in 5 ml of dichloromethane. 1.227 g of crude acetic acid (1RS,3RS,4RS)-4-{[1-(2,6-dimethoxy-pyridin-3-yl)methanoyl]amino}-3-(3-ethoxy-4-methoxyphenyl)cyclohexyl ester (compound A1) dissolved in 15 ml of dichloromethane are added and the reaction mixture stirred at room temperature over night. The reaction mixture is cooled with an ice bath and 20 ml of triethylamine are added, than cautiously 10 ml of water with vigorous stirring. The organic layer is separated, concentrated and the crude product purified by flash chromatography to give 715 mg of the title compound.

EF: $C_{25}H_{30}N_2O_6$; MW: calc.: 454,53.
MS: fnd.: 455.2 (MH$^+$).

Starting from the appropriate compounds, which are mentioned or described explicity below (compound A2 to A17) the following compounds are obtained according to the procedure as in compound 18 or analogously or similarly thereto. If necessary, the cyclization reaction can be carried out in the presence of a catalytic amount of a Lewis acid such as e.g. tin tetrachloride.

19. Acetic acid (2R,4aR,10bR)-9-ethoxy-8-methoxy-6-pyrimidin-5-yl-1,2,3,4,4a, 10b-hexahydro-phenanthridin-2-yl ester
EF: $C_{22}H_{25}N_3O_4$; MW: calc.: 395,46.
MS: fnd.: 396,3.

20. Acetic acid (2R,4aR,10bR)-9-ethoxy-8-methoxy-6-(6-pyrazol-1-yl-pyridin-3-yl)-1,2,3,4,4a, 10b-hexahydro-phenanthridin-2-yl ester
EF: $C_{26}H_{28}N_4O_4$; MW: calc.: 460,54.
MS: fnd.: 461,3.

21. Acetic acid (2R,4aR,10bR)-9-ethoxy-8-methoxy-6-(2-methoxy-pyrimidin-5-yl)-1,2,3,4,4a, 10b-hexahydro-phenanthrldin-2-yl ester
EF: $C_{23}H_{27}N_3O_5$; MW: calc.: 425,49.
MS: fnd.: 426,3.

22. Acetic acid (2R,4aR,10bR)-6-(2,4-dimethoxy-pyrimidin-5-yl)-9-ethoxy-8-methoxy-1,2,3,4,4a, 10b-hexahydro-phenanthridin-2-yl ester
EF: $C_{24}H_{29}N_3O_6$; MW: calc.: 455,52.
MS: fnd.: 456,3.

23. Acetic acid (2R,4aR,10bR)-9-ethoxy-6-(6-imidazol-1-yl-pyridin-3-yl)-8-methoxy-1,2,3,4,4a, 10b-hexahydro-phenanthridin-2-yl ester
EF: $C_{26}H_{28}N_4O_4$; MW: calc.: 460,55.
MS: fnd.: 461,3.

24. Acetic acid (2R,4aR,10bR)-9-ethoxy-8-methoxy-6-pyrazin-2-yl-1,2,3,4,4a, 10b-hexahydro-phenanthridin-2-yl ester
EF: $C_{22}H_{25}N_3O_4$; MW: calc.: 395,46.
MS: fnd.: 396,3.

25. Acetic acid (2R,4aR,10bR)-6-(2,6-dimethoxy-pyridin-3-yl)-9-ethoxy-8-methoxy-1,2,3,4,4a, 10b-hexahydro-phenanthridin-2-yl ester
EF: $C_{25}H_{30}N_2O_6$; MW: calc.: 454,53.
MS: fnd.: 455,3.

26. Acetic acid (2R,4aR,10bR)-9-ethoxy-8-methoxy-6-(1-methyl-6-oxo-1,6-dihydro-pyridin-3-yl)-1,2,3,4,4a, 10b-hexahydro-phenanthridin-2-yl ester
$C_{24}H_{28}N_2O_5$
Calc.: 424.50.
Found (MH$^+$): 425.3.

27. Acetic acid (2R,4aR,10bR)-9-ethoxy-8-methoxy-6-(6-methoxy-pyridin-3-yl)-1,2,3,4,4a, 10b-hexahydro-phenanthridin-2-yl ester
$C_{24}H_{28}N_2O_5$
Calc.: 424.50.
Found (MH$^+$): 425.2.

28. Acetic acid (2R,4aR,10bR)-6-(2-dimethylamino-4-methoxy-pyrimidin-5-yl)-9-ethoxy-8-methoxy-1,2,3,4,4a, 10b-hexahydro-phenanthridin-2-yl ester
$C_{25}H_{32}N_4O_5$
Calc.: 468.56.
Found (MH$^+$): 469.3.

29. Acetic acid (2R,4aR,10bR)-6-(4,6-dimethoxy-pyridin-3-yl)-9-ethoxy-8-methoxy-1,2,3,4,4a, 10b-hexahydro-phenanthridin-2-yl ester
$C_{25}H_{30}N_2O_6$
Calc.: 454.53.
Found (MH$^+$): 455.3.

30. Acetic acid (2R,4aR,10bR)-6-(2-dimethylamino-pyrimidin-5-yl)-9-ethoxy-8-methoxy-1,2,3,4,4a, 10b-hexahydro-phenanthridin-2-yl ester
$C_{24}H_{30}N_4O_4$
Calc.: 438.53.
Found (MH$^+$): 439.3.

31. Acetic acid (2R,4aR,10bR)-9-ethoxy-8-methoxy-6-(1-methyl-2-oxo-1,2-dihydro-pyrimidin-5-yl)-1,2,3,4,4a, 10b-hexahydro-phenanthridin-2-yl ester
$C_{23}H_{27}N_3O_5$
Calc.: 425.49.

32. Acetic acid (2R,4aR,10bR)-6-(3,6-dimethoxy-pyridazin-4-yl)-9-ethoxy-8-methoxy-1,2,3,4,4a, 10b-hexahydro-phenanthridin-2-yl ester
$C_{24}H_{29}N_3O_6$
Calc.: 455.52.
Found (MH$^+$): 456.3.

33. Acetic acid (2R,4aR,10bR)-6-(5,6-dimethoxy-pyridin-3-yl)-9-ethoxy-8-methoxy-1,2,3,4,4a, 10b-hexahydro-phenanthridin-2-yl ester
$C_{25}H_{30}N_2O_6$
Calc.: 454.53.

34. Acetic acid (2R,4aR,10bR)-9-ethoxy-8-methoxy-6-(2-methylsulfanyl-pyrimidin-5-yl)-1,2,3,4,4a, 10b-hexahydro-phenanthridin-2-yl ester
$C_{23}H_{27}N_3O_4S$
Calc.: 441.55.

Starting Materials

A1. Acetic acid (1RS,3RS,4RS)-4-{[1-(2,6-dimethoxy-pyridin-3-yl)methanoyl]amino}-3-(3-ethoxy-4-methoxyphenyl)cyclohexyl ester 555 mg of 2,6-dimethoxynicotinic acid and 581 mg of N-ethyl-N'-(3-dimethylaminopropyl)carbodiimide hydrochloride are placed in a flask under nitrogen. 778 mg of acetic acid (1RS,3RS,4RS)-4-amino-3-(3-ethoxy-4-methoxyphenyl)cyclohexyl ester (compound B1) and 2 mg of 4-dimethylaminopyridine both as solution in dichloromethane are added and the solution stirred for 1 h at 40° C., than 42 h at room temperature. The reaction is quenched with 5 ml of water. After phase separation the organic layer is washed with 2.5 ml of saturated potassium hydrogencarbonate solution. After drying the organic layer with magnesium sulfate the solvent is removed to give 1.227 g of the crude title compound which are used for the following step without further purification.

MW: calc.: 472.54. MS: fnd: 473.1.

The following compounds can be prepared from the starting compound B1a and the appropriate commercially available or art-known heteroaryl carboxylic acids in a manner according to compound A1 or analogously or similarly thereto.

A2. Acetic acid (1R,3R,4R)-3-(3-ethoxy-4-methoxy-phenyl)-[(1-pyrimidin-5-yl-methanoyl)-amino]-cyclohexyl ester
MW calc.: 413.48. MS: fnd: 414.1.

A3. Acetic acid (1R,3R,4R)-3-(3-ethoxy-4-methoxy-phenyl)-4-{[1-(6-pyrazol-1-yl-pyridin-3-yl)-methanoyl]-amino}-cyclohexyl ester
MW calc.: 478.55.

A4. Acetic acid (1R,3R,4R)-3-(3-ethoxy-4-methoxy-phenyl)-4-{[1-(2-methoxy-pyrimidin-5-yl)-methanoyl]-amino}-cyclohexyl ester
MW calc.: 443.50. MS: fnd: 444.2.

A5. Acetic acid (1R,3R,4R)-4-{[1-(2,4-dimethoxy-pyrimidin-5-yl)-methanoyl]-amino}-3-(3-ethoxy-4-methoxy-phenyl)-cyclohexyl ester
MW calc.: 473.53. MS: fnd: 474.2.

A6. Acetic acid (1R,3R,4R)-3-(3-ethoxy-4-methoxy-phenyl)-4-{[1-(6-imidazol-1-yl-pyridin-3-yl)-methanoyl]-amino}-cyclohexyl ester
MW calc.: 478.55. MS: fnd: 479.3.

A7. Acetic acid (1R,3R,4R)-3-(3-ethoxy-4-methoxy-phenyl)-4-[(1-pyrazin-2-yl-methanoyl)-amino]-cyclohexyl ester
MW calc.: 413.48. MS: fnd: 414.2.

A8. Acetic acid (1R,3R,4R)-4-{[1-(2,6-dimethoxy-pyridin-3-yl)-methanoyl]-amino}-3-(3-ethoxy-4-methoxy-phenyl)-cyclohexyl ester
MW calc.: 472.54. MS: fnd: 473.2.

A9. Acetic acid (1R,3R,4R)-3-(3-ethoxy-4-methoxy-phenyl)-4-{[1-(1-(1-methyl-6-oxo-1,6-dihydro-pyridin-3-yl)-methanoyl]-amino}-cyclohexyl ester A10. Acetic acid (1R,3R,4R)-3-(3-ethoxy-4-methoxy-phenyl)-4-{[1-(6-methoxy-pyridin-3-yl)-methanoyl]-amino}-cyclohexyl ester A11. Acetic acid (1R,3R,4R)-4-{([1-(2-dimethylamino-4-methoxy-pyrimidin-5-yl)-methanoyl]-amino}-3-(3-ethoxy-4-methoxy-phenyl)-cyclohexyl ester A12. Acetic acid (1R,3R,4R)-4-{[1-(4,6-dimethoxy-pyridin-3-yl)-methanoyl]-amino}-3-(3-ethoxy-4-methoxy-phenyl)-cyclohexyl ester A13. Acetic acid (1R,3R,4R)-4-{[1-(2-dimethylamino-pyrimidin-5-yl)-methanoyl]-amino}-3-(3-ethoxy-4-methoxy-phenyl)-cyclohexyl ester A14. Acetic acid (1R,3R,4R)-3-(3-ethoxy-4-methoxy-phenyl)-4-{[1-(1-methyl-2-oxo-1,2-dihydro-pyrimidin-5-yl)-methanoyl]-amino}-cyclohexyl ester A15. Acetic acid (1R,3R,4R)-3-(3-ethoxy-4-methoxy-phenyl)-4-{[1-(3,6-dimethoxy-pyridazin-4-yl)-methanoyl]-amino}-cyclohexyl ester A16. Acetic acid (1R,3R,4R)-4-{[1-(5,6-dimethoxy-pyridin-3-yl)-methanoyl]-amino}-3(3-ethoxy-4-methoxy-phenyl)-cyclohexyl ester A17. Acetic acid (1R,3R,4R)-4-{[1-(2-methylsulfanyl-pyrimidin-5-yl)-methanoyl]-amino}-3-(3-ethoxy-4-methoxy-phenyl)-cyclohexyl ester B1. Acetic acid (1RS,3RS,4RS)-4-amino-3-(3-ethoxy-4-methoxy-phenyl)-cyclohexyl ester Starting from compound C1 mentioned below, the title compound is obtained analogously to the procedure as in Example B2.

EF: $C_{17}H_{25}NO_4$; MW: 307.39.

MS: 308.0 (MH$^+$).

B1a. Acetic acid (1R,3R,4R)-4-amino-3-(3-ethoxy-4-methoxy-phenyl)-cyclohexyl ester 24.0 g (55.0 mmol) of the pyroglutamate of the title compound (compound B1b) are suspended in 150 ml of water, 100 ml of dichloromethane are added, then saturated KHCO$_3$-solution until the gas evolution ceased. After phase separation, reextraction of the water layer and drying the combined organic layers with sodium sulfate the solvent is removed to give 16.9 g of the salt-free title compound. Analytical Column Chromatography (CHIRALPAK AD-H 250× 4.6 mm 5 µ No.ADH0CE-DB030, Eluent: n-Hexan/iPrOH=80/20 (v/v)+0.1% Diethylamine): Retention Time: 6.54 min B1b. Acetic acid (1R,3R,4R)-4-amino-3-(3-ethoxy-4-methoxy-phenyl)-cyclohexyl ester, salt with L-pyroglutamic acid Solution A: 55.2 9 (180 mmol) of racemic acetic acid (1RS,3RS,4RS)-4-amino-3-(3-ethoxy-4-methoxy-phenyl)-cyclohexyl ester (compound B1) are dissolved in 540 ml of isopropyl acetate.

Solution B: 18.6 g (144 mmol) of L-pyroglutamic acid are dissolved in 260 ml of isopropanol under heating, then 290 ml of isopropyl acetate is added carefully.

Solution B is added to solution A and left for 48 hours. The solid is filtered off and washed with a little isopropyl acetate to give after drying 32.48 g colorless crystals with a ratio of the enantiomers of 97:3 in favour of the title compound.

M.p.: 165-167° C.

B2. Acetic acid (1RS,3RS,4RS)-4-amino-3-(3,4-dimethoxyphenyl)cyclohexyl ester

A solution of 10.37 g of acetic acid (1RS,3RS,4RS)-3-(3,4-dimethoxyphenyl)-4-nitrocyclohexyl ester (compound C2) in 240 ml of ethanol is added to a zinc-copper couple, prepared from 16.8 g of zinc powder and 920 mg of copper (II) acetate monohydrate in acetic acid, the resulting suspension is refluxed and treated with 26 ml of acetic acid, 3.2 ml of water and 26 ml of ethanol. The resulting mixture is refluxed for further 15 min. The precipitate is filtered off with suction and the solvent is removed. Chromatographical purification on silica gel using a mixture of petroleum ether/ethyl acetate/triethylamine in the ratio 2/7/1 and concentration of the corresponding eluate fractions afford 5.13 g (55% of theory) of the title compound as a pale brown oil.

$R_f$=0.35 (petroleum ether/ethyl acetate/triethylamine=2/7/1)

C1. Acetic acid (1RS,3RS,4RS)-3-(3-ethoxy-4-methoxy-phenyl)-4-nitrocyclohexyl ester Starting from compound D1 mentioned below, the title compound is obtained according to the procedure as in the reference compound C2.

C2. Acetic acid (1RS,3RS,4RS)-3-(3,4-dimethoxyphenyl)-4-nitrocyclohexyl ester 10.18 g of (1RS,3RS,4RS)-3-(3,4-dimethoxyphenyl)-4-nitrocyclohexanol (compound D2) are dissolved in 100 ml of acetic anhydride and the solution is heated to 100° C. for 1-2 h. After removal of the solvent, the residue is chromatographed on silica gel using a mixture of petroleum ether/ethyl acetate in the ratio 2/1. Concentration of the corresponding eluate fractions furnish 10.37 g (89% of theory) of the title compound as an oil.

$R_f$=0.32 (petroleum ether/ethyl acetate=2/1)

D1. (1RS,3RS,4RS)-3-(3-Ethoxy-4-methoxy-phenyl)-4-nitrocyclohexanol

Starting from compound E1 mentioned below, the title compound is obtained according to the procedure as in the reference compound D2.

D2. (1RS,3RS,4RS)-3-(3,4-Dimethoxyphenyl)-4-nitrocyclohexanol 10 g of (1RS,3RS,4SR)-3-(3,4-dimethoxyphenyl)-4-nitrocyclohexanol (compound E2) are dissolved in 170 ml of absolute 1,2-dimethoxyethane. 14.3 ml of a 30% solution of sodium methanolate in methanol are added dropwise. After complete addition, stirring is continued for 10 min and a mixture consisting of 85% phosphoric acid and methanol is added to pH 1. By adding of saturated potassium hydrogencarbonate solution the resulting suspension is neutralized. The mixture is diluted with water and dichloromethane, the organic layer is separated and extracted with dichloromethane. The solvents are removed under reduced pressure to yield the title compound as a pale yellow oil, which crystallizes. The title compound is used without further purification in the next step.

$R_f$=0.29 (petroleum ether/ethyl acetate=1/1)

M.p.: 126-127° C.

E1. (1RS,3RS,4SR)-3-(3-Ethoxy-4-methoxy-phenyl)-4-nitrocyclohexanol

Starting from compound F1 mentioned below, the title compound is obtained according to the procedure as in the reference compound E2.

E2. (1RS,3RS,4SR)-3-(3,4-Dimethoxyphenyl)-4-nitrocyclohexanol

Under nitrogen atmosphere 16.76 g of (3RS,4SR)-3-(3,4-dimethoxyphenyl)-4-nitrocyclohexanone (compound F2) are dissolved in 300 ml of tetrahydrofurane, the solution is cooled to −78° C., and 75 ml of 1 M solution of potassium tri-sec-butylborohydride in tetrahydrofurane is added dropwise. After stirring for further 1 h, a mixture consisting of 30% hydrogeneperoxide solution and phosphate buffer solution is added. Stirring is continued for further 10 min, the reaction mixture is diluted with 400 ml of ethyl acetate and the aqueous layer is extracted with ethyl acetate, the combined organic phases are concentrated to give a foam, which is purified by chromatography on silica gel using a mixture of petroleum ether/ethyl acetate in the ratio 1/1 to furnish 10.18 g (60% of theory) of the title compound.

EF: $C_{14}H_{19}NO_5$; MW: 281.31

MS: 299.1 ($MNH_4^+$)

$R_f$=0.29 (petroleum ether/ethyl acetate=1/1)

M.p.: 139-141° C.

F1. (3RS,4SR)-3-(3-Ethoxy-4-methoxy-phenyl)-4-nitrocyclohexanone

Starting from compound G1 mentioned below, the title compound is obtained according to the procedure as in the reference compound F2.

F2. (3RS,4SR)-3-(3,4-Dimethoxyphenyl)-4-nitrocyclohexanone 90.0 g of 3,4-dimethoxy-ω-nitrostyrene (compound G2), 90 ml of 2-trimethylsilyloxy-1,3-butadiene and 180 ml of abs. Toluene are put in an autoclave, where the mixture is stirred at 140° C. for 2 days and then cooled. After addition of 1000 ml of ethyl acetate, 300 ml of a 2 N solution of hydrochloric acid are dropped under stirring. The phases are separated and the aqueous layer is extracted three times with dichloromethane. The combined organic extracts are washed with saturated sodium hydrogen-carbonate solution, dried over magnesium sulfate and the solvents are removed under reduced pressure to give 150 g of the crude title compound. Further purification is carried out by chromatography on silica gel using petroleum ether/ethyl acetate in the ratio 1/1 as eluent to give 81.5 g (67% of theory) of the pure title compound.

EF: $C_{14}H_{17}NO_5$; MW: 279.30

MS: 279 ($M^+$), 297.1 ($MNH_4^+$)

$R_f$=0.47 (petroleum ether/ethyl acetate=1/1)

M.p.: 147-148° C.

G1. 3-Ethoxy-4-methoxy-ω-nitrostyrene

Starting from art-known starting compounds, the title compound is obtained according to the procedure as in the reference compound G2:

G2. 3,4-Dimethoxy-ω-nitrostyrene 207.0 g of 3,4-dimethoxybenzaldehyde, 100.0 g of ammonium acetate and 125 ml of nitromethane are heated to boiling for 3-4 h in 1.0 l of glacial acetic acid. After cooling in an ice bath, the precipitate is filtered off with suction, rinsed with glacial acetic acid and petroleum ether and dried. M.p.: 140-141° C.

Yield: 179.0 g.

Commercial Utility

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinits/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus and conditions associated with cerebral metabolic inhibition, such as cerebral senility, senile dementia (Alzheimer's disease), memory impairment associated with Parkinson's disease or multiinfarct dementia; and also illnesses of the central nervous system, such as depressions or arteriosclerotic dementia; as well as for enhancing cognition. Yet in addition, the compounds of the invention are useful in the treatment of diabetes mellitus, leukaemia and osteoporosis.

In the context of their properties, functions and usabilities mentioned herein, the compounds according to the present invention are expected to be distinguished by valuable and desirable effects related therewith, such as e.g. any beneficial effects related with their therapeutic and pharmaceutical suitability.

Compounds according to this invention, especially when they are in crystalline form, are expected to have desirable physicochemical properties and such properties may beneficially influence, for example, the stability (such as e.g., without being limited thereto, the thermal stability or the hygroscopic stability or the like), as well as the chemical and pharmaceutical processing, formulating and mechanical handling on a commercial scale. Thus, these crystalline compounds may be particularly suited for the manufacture of commercially viable and pharmaceutically acceptable drug compositions or dosage forms.

The present invention provides compounds according to this invention in crystalline form.

Also, the present invention provides compounds according to this invention isolated in purified or substantially pure form, such as e.g. greater than about 50%, more precisely about 60%, more precisely about 70%, more precisely about 80%, more precisely about 90%, more precisely about 95%, more precisely about 97%, more precisely about 99% wt purity as determined by art-known methods.

Also, the present invention provides compounds according to this invention in a pharmaceutically acceptable form.

Also, the present invention provides compounds according to this invention in solid or liquid pharmaceutically acceptable dosage forms, particularly solid oral dosage forms, such as tablets and capsules, as well as suppositories and other pharmaceutical dosage forms.

The invention further relates to a method for the treatment of mammals, including humans, which are suffering from one of the above mentioned illnesses. The method is characterized in that a pharmacologically active and therapeutically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention also relates to the use of the compounds according to the invention for the production of pharmaceutical compositions for treating disorders which are mediated by phosphodiesterases, in particular PDE4-mediated disorders, such as, for example, those mentioned in the specification of this invention or those which are apparent or known to the skilled person.

The invention also relates to the use of the compounds according to the invention for the manufacture of pharmaceutical compositions having PDE4 inhibitory activity.

The invention furthermore relates to pharmaceutical compositions for the treatment and/or prophylaxis of the illnesses mentioned comprising one or more of the compounds according to the invention.

The invention yet furthermore relates to compositions comprising one or more compounds according to this invention and pharmaceutically acceptable auxiliaries and/or excipients.

The invention yet furthermore relates to compositions comprising one or more compounds according to this invention and a pharmaceutically acceptable carrier. Said compositions can be used in therapy, such as e.g. for treating, preventing or ameliorating one or more of the abovementioned diseases.

The invention still yet furthermore relates to pharmaceutical compositions according to this invention having PDE, particularly PDE4, inhibitory activity.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds according to the invention. The packaging material, label and package insert otherwise parallel or resemble what is generally regarded as standard packaging material, labels and package inserts for pharmaceuticals having related utilities.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, excipients, carriers, vehicles, diluents or adjuvants which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 μm, advantageously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1-99%. The dose for administration by inhalation is customarily between 0.01 and 3 mg per day. The customary dose in the case of systemic therapy (p.o. or i.v.) is between 0.003 and 3 mg/kg per day. In another embodiment, the dose for administration by inhalation is between 0.1 and 3 mg per day, and the dose in the case of systemic therapy (p.o. or i.v.) is between 0.03 and 3 mg/kg per day.

Biological Investigations

The second messenger cyclic AMP (CAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21-40, "The Handbook of Immunopharmacology", Academic Press, 1996), and its inhibition leads to an increase of the intracellular CAMP concentration and thus to the inhibition of cellular activation (JE Souness et al., Immunopharmacology 47:127-162, 2000).

The antiinflammatory potential of PDE4 inhibitors in vivo in various animal models has been described (M M Teixeira, TiPS 18: 164-170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682-690, 1991) or eosinophilic (A Hatzelmann et al., Brit J Pharmacol 114: 821-831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221-231, 1997, and Pulmonary Pharmacol Therap 12: 377-386,1999). In addition, the immunomodulatory potential of PDE4 inhibitors is evident from the inhibition of T-cell responses like cytokine synthesis or proliferation (DM Essayan, Biochem Pharmacol 57: 965-973, 1999). Substances which inhibit the secretion of the aforementioned proinflammatory mediators are those which inhibit PDE4. PDE4 inhibition by the compounds according to the invention is thus a central indicator for the suppression of inflammatory processes.

Methods for Measuring Inhibition of PDE4 Activity

The PDE4B2 (GB no. M97515) was a gift of Prof. M. Conti (Stanford University, USA). It was amplified from the original plasmid (pCMV5) via PCR with primers Rb9 (5'-GC-CAGCGTGCAAATMT-GMGG-3') and Rb10 (5'-AGAGGGGGATTATGTATCCAC-3') and cloned into the pCR-Bac vector (Invitrogen, Groningen, N L).

The recombinant baculovirus was prepared by means of homologous recombination in SF9 insect cells. The expression plasmid was cotransfected with Bac-N-Blue (Invitrogen, Groningen, N L) or Baculo-Gold DNA (Pharmingen, Hamburg) using a standard protocol (Pharmingen, Hamburg). Wt virus-free recombinant virus supernatant was selected using plaque assay methods. After that, high-titre virus supernatant was prepared by amplifying 3 times. PDE was expressed in SF21 cells by infecting $2 \times 10^6$ cells/ml with an MOI (multiplicity of infection) between 1 and 10 in serum-free SF900 medium (Life Technologies, Paisley, UK). The cells were cultured at 28° C. for 48-72 hours, after which they were pelleted for 5-10 min at 1000 g and 4° C.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 10 mM β-mercaptoethanol, 2 mM benzamidine, 0.4 mM Pefablock, 10 μM leupeptin, 10 μM pepstatin A, 5 μM trypsin inhibitor) and disrupted by ultrasonication. The homogenate was then centrifuged for 10 min at 1000×g and the supernatant was stored at −80° C. until subsequent use (see below). The protein content was determined by the Bradford method (BioRad, Munich) using BSA as the standard.

PDE4B2 activity is inhibited by the said compounds in a modified SPA (scintillation proximity assay) test, supplied by Amersham Biosciences (see procedural instructions "phosphodiesterase [3H]cAMP SPA enzyme assay, code TRKQ 7090"), carried out in 96-well microtiter plates (MTP's). The test volume is 100 µl and contains 20 mM Tris buffer (pH 7.4), 0.1 mg of BSA (bovine serum albumin)/ml, 5 mM $Mg^{2+}$, 0.5 µM cAMP (including about 50,000 cpm of [3H]cAMP), 1 µl of the respective substance dilution in DMSO and sufficient recombinant PDE (1000×g supernatant, see above) to ensure that 10-20% of the cAMP is converted under the said experimental conditions. The final concentration of DMSO in the assay (1% v/v) does not substantially affect the activity of the PDE investigated. After a preincubation of 5 min at 37° C., the reaction is started by adding the substrate (cAMP) and the assay is incubated for a further 15 min; after that, it is stopped by adding SPA beads (50 µl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE activity are determined from the concentration-effect curves by means of non-linear regression.

The invention claimed is:
1. A salt selected from the group consisting of
(2R,4aR,10bR)-6-(2,6-Dimethoxy-pyridin-3-yl)-9-ethoxy-8-methoxy-1,2,3,4,4a,10b-hexahydro-phenanthridin-2-ol hydrochloride;
(2R,4aR,10bR)-9-Ethoxy-8-methoxy-6-pyrimidin-5-yl-1,2,3,4,4a,10b-hexahydro-phenanthridin-2-ol hydrochloride;
(2R,4aR,10bR)-9-Ethoxy-8-methoxy-6-(6-pyrazol-1-yl-pyridin-3-yl)-1,2,3,4,4a,10b-hexahydro-phenanthridin-2-ol hydrochloride;
(2R,4aR,10bR)-9-Ethoxy-8-methoxy-6-(2-methoxy-pyrimidin-5-yl)-1,2,3,4,4a,10b-hexahydro-phenanthridin-2-ol hydrochloride;
(2R,4aR,10bR)-6-(2,4-Dimethoxy-pyrimidin-5-yl)-9-ethoxy-8-methoxy-1,2,3,4,4a,10b-hexahydro-phenanthridin-2-ol hydrochloride;
(2R,4aR,10bR)-9-Ethoxy-8-methoxy-6-pyrazin-2-yl-1,2,3,4,4a,10b-hexahydro-phenanthridin-2-ol hydrochloride;
(2R,4aR,10bR)-6-(3,6-Dimethoxy-pyridazin-4-yl)-9-ethoxy-8-methoxy-1,2,3,4,4a,10b-hexahydro-phenanthridin-2-ol hydrochloride;
(2R,4aR,10bR)-9-Ethoxy-8-methoxy-6-(6-methoxy-pyridin-3-yl)-1,2,3,4,4a,10b-hexahydro-phenanthridin-2-ol hydrochloride;
(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol hydrochloride;
(2R,4aR,10bR)-6-(4,6-Dimethoxy-pyridin-3-yl)-9-ethoxy-8-methoxy-1,2,3,4,4a,10b-hexahydro-phenanthridin-2-ol hydrochloride;
(2R,4aR,10bR)-6-(2-Dimethylamino-pyrimidin-5-yl)-9-ethoxy-8-methoxy-1,2,3,4,4a,10b-hexahydro-phenanthridin-2-ol hydrochloride;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one hydrochloride;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one hydrochloride;
(2R,4aR,10bR)-6-(2,6-Dimethoxy-pyridin-3-yl)-9-ethoxy-8-methoxy-1,2,3,4,4a,10b-hexahydro-phenanthridin-2-ol sulfate;
(2R,4aR,10bR)-9-Ethoxy-8-methoxy-6-(2-methoxy-pyrimidin-5-yl)-1,2,3,4,4a,10b-hexahydro-phenanthridin-2-ol sulfate;
(2R,4aR,10bR)-6-(2,4-Dimethoxy-pyrimidin-5-yl)-9-ethoxy-8-methoxy-1,2,3,4,4a,10b-hexahydro-phenanthridin-2-ol sulfate;
(2R,4aR,10bR)-9-Ethoxy-6-(6-imidazol-1-yl-pyridin-3-yl)-8-methoxy-1,2,3,4,4a,10b-hexahydro-phenanthridin-2-ol sulfate;
(2R,4aR,10bR)-6-(3,6-Dimethoxy-pyridazin-4-yl)-9-ethoxy-8-methoxy-1,2,3,4,4a,10b-hexahydro-phenanthridin-2-ol sulfate;
(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol sulfate;
(2R,4aR,10bR)-6-(4,6-Dimethoxy-pyridin-3-yl)-9-ethoxy-8-methoxy-1,2,3,4,4a,10b-hexahydro-phenanthridin-2-ol sulfate;
(2R,4aR,10bR)-6-(2-Dimethylamino-pyrimidin-5-yl)-9-ethoxy-8-methoxy-1,2,3,4,4a,10b-hexahydro-phenanthridin-2-ol sulfate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one sulfate;
(2R,4aR,10bR)-9-Ethoxy-8-methoxy-6-pyrimidin-5-yl-1,2,3,4,4a,10b-hexahydro-phenanthridin-2-ol methansulfonate;
(2R,4aR,10bR)-9-Ethoxy-8-methoxy-6-(2-methoxy-pyrimidin-5-yl)-1,2,3,4,4a,10b-hexahydro-phenanthridin-2-ol methansulfonate;
(2R,4aR,10bR)-6-(2,4-Dimethoxy-pyrimidin-5-yl)-9-ethoxy-8-methoxy-1,2,3,4,4a,10b-hexahydro-phenanthridin-2-ol methansulfonate;
(2R,4aR,10bR)-9-Ethoxy-6-(6-imidazol-1-yl-pyridin-3-yl)-8-methoxy-1,2,3,4,4a,10b-hexahydro-phenanthridin-2-ol methansulfonate;
(2R,4aR,10bR)-9-Ethoxy-8-methoxy-6-pyrazin-2-yl-1,2,3,4,4a,10b-hexahydro-phenanthridin-2-ol methansulfonate;
(2R,4aR,10bR)-6-(3,6-Dimethoxy-pyridazin-4-yl)-9-ethoxy-8-methoxy-1,2,3,4,4a,10b-hexahydro-phenanthridin-2-ol methansulfonate;
(2R,4aR,10bR)-9-Ethoxy-8-methoxy-6-(6-methoxy-pyridin-3-yl)-1,2,3,4,4a,10b-hexahydro-phenanthridin-2-ol methansulfonate;
(2R,4aR,10bR)-6-(4,6-Dimethoxy-pyridin-3-yl)-9-ethoxy-8-methoxy-1,2,3,4,4a,10b-hexahydro-phenanthridin-2-ol methansulfonate;
(2R,4aR,10bR)-6-(2-Dimethylamino-pyrimidin-5-yl)-9-ethoxy-8-methoxy-1,2,3,4,4a,10b-hexahydro-phenanthridin-2-ol methansulfonate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one methansulfonate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one methansulfonate;
(2R,4aR,10bR)-6-(2,6-Dimethoxy-pyridin-3-yl)-9-ethoxy-8-methoxy-1,2,3,4,4a,10b-hexahydro-phenanthridin-2-ol citrate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol citrate;

(2R,4aR,10bR)-9-Ethoxy-8-methoxy-6-(2-methoxy-pyrimidin-5-yl)-1,2,3,4,4a,10b-hexahydro-phenanthridin-2-ol citrate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol citrate;

(2R,4aR,10bR)-9-Ethoxy-6-(6-imidazol-1-yl-pyridin-3-yl)-8-methoxy-1,2,3,4,4a,10b-hexahydro-phenanthridin-2-ol citrate;

(2R,4aR,10bR)-6-(3,6-Dimethoxy-pyridazin-4-yl)-9-ethoxy-8-methoxy-1,2,3,4,4a,10b-hexahydro-phenanthridin-2-ol citrate;

(2R,4aR,10bR)-9-Ethoxy-8-methoxy-6-(6-methoxy-pyridin-3-yl)-1,2,3,4,4a,10b-hexahydro-phenanthridin-2-ol citrate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol citrate;

(2R,4aR,10bR)-6-(4,6-Dimethoxy-pyridin-3-yl)-9-ethoxy-8-methoxy-1,2,3,4,4a,10b-hexahydro-phenanthridin-2-ol citrate;

(2R,4aR,10bR)-6-(2-Dimethylamino-pyrimidin-5-yl)-9-ethoxy-8-methoxy-1,2,3,4,4a,10b-hexahydro-phenanthridin-2-ol citrate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one citrate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one citrate;

(2R,4aR,10bR)-6-(2,6-Dimethoxy-pyridin-3-yl)-9-ethoxy-8-methoxy-1,2,3,4,4a,10b-hexahydro-phenanthridin-2-ol L-tartrate;

(2R,4aR,10bR)-9-Ethoxy-8-methoxy-6-pyrimidin-5-yl-1,2,3,4,4a,10b-hexahydro-phenanthridin-2-ol L-tartrate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol L-tartrate;

(2R,4aR,10bR)-9-Ethoxy-8-methoxy-6-(2-methoxy-pyrimidin-5-yl)-1,2,3,4,4a,10b-hexahydro-phenanthridin-2-ol L-tartrate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol L-tartrate;

(2R,4aR,10bR)-9-Ethoxy-8-methoxy-6-pyrazin-2-yl-1,2,3,4,4a,10b-hexahydro-phenanthridin-2-ol L-tartrate;

(2R,4aR,10bR)-6-(3,6-Dimethoxy-pyridazin-4-yl)-9-ethoxy-8-methoxy-1,2,3,4,4a,10b-hexahydro-phenanthridin-2-ol L-tartrate;

(2R,4aR,10bR)-9-Ethoxy-8-methoxy-6-(6-methoxy-pyridin-3-yl)-1,2,3,4,4a,10b-hexahydro-phenanthridin-2-ol L-tartrate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol L-tartrate;

(2R,4aR,10bR)-6-(4,6-Dimethoxy-pyridin-3-yl)-9-ethoxy-8-methoxy-1,2,3,4,4a,10b-hexahydro-phenanthridin-2-ol L-tartrate;

(2R,4aR,10bR)-6-(2-Dimethylamino-pyrimidin-5-yl)-9-ethoxy-8-methoxy-1,2,3,4,4a,10b-hexahydro-phenanthridin-2-ol L-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one L-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one L-tartrate;

(2R,4aR,10bR)-6-(2,6-Dimethoxy-pyridin-3-yl)-9-ethoxy-8-methoxy-1,2,3,4,4a,10b-hexahydro-phenanthridin-2-ol D-tartrate;

(2R,4aR,10bR)-9-Ethoxy-8-methoxy-6-(2-methoxy-pyrimidin-5-yl)-1,2,3,4,4a,10b-hexahydro-phenanthridin-2-ol D-tartrate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol D-tartrate;

(2R,4aR,10bR)-9-Ethoxy-6-(6-imidazol-1-yl-pyridin-3-yl)-8-methoxy-1,2,3,4,4a,10b-hexahydro-phenanthridin-2-ol D-tartrate;

(2R,4aR,10bR)-9-Ethoxy-8-methoxy-6-pyrazin-2-yl-1,2,3,4,4a,10b-hexahydro-phenanthridin-2-ol D-tartrate;

(2R,4aR,10bR)-6-(3,6-Dimethoxy-pyridazin-4-yl)-9-ethoxy-8-methoxy-1,2,3,4,4a,10b-hexahydro-phenanthridin-2-ol D-tartrate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-tartrate;

(2R,4aR,10bR)-6-(4,6-Dimethoxy-pyridin-3-yl)-9-ethoxy-8-methoxy-1,2,3,4,4a,10b-hexahydro-phenanthridin-2-ol D-tartrate;

(2R,4aR,10bR)-6-(2-Dimethylamino-pyrimidin-5-yl)-9-ethoxy-8-methoxy-1,2,3,4,4a,10b-hexahydro-phenanthridin-2-ol D-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one D-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one D-tartrate;

(2R,4aR,10bR)-6-(2,6-Dimethoxy-pyridin-3-yl)-9-ethoxy-8-methoxy-1,2,3,4,4a,10b-hexahydro-phenanthridin-2-ol meso-tartrate;

(2R,4aR,10bR)-9-Ethoxy-8-methoxy-6-pyrimidin-5-yl-1,2,3,4,4a,10b-hexahydro-phenanthridin-2-ol meso-tartrate;

(2R,4aR,10bR)-9-Ethoxy-8-methoxy-6-(2-methoxy-pyrimidin-5-yl)-1,2,3,4,4a,10b-hexahydro-phenanthridin-2-ol meso-tartrate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol meso-tartrate;

(2R,4aR,10bR)-9-Ethoxy-6-(6-imidazol-1-yl-pyridin-3-yl)-8-methoxy-1,2,3,4,4a,10b-hexahydro-phenanthridin-2-ol meso-tartrate;

(2R,4aR,10bR)-9-Ethoxy-8-methoxy-6-pyrazin-2-yl-1,2,3,4,4a,10b-hexahydro-phenanthridin-2-ol meso-tartrate;

(2R,4aR,10bR)-6-(3,6-Dimethoxy-pyridazin-4-yl)-9-ethoxy-8-methoxy-1,2,3,4,4a,10b-hexahydro-phenanthridin-2-ol meso-tartrate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol meso-tartrate;

(2R,4aR,10bR)-6-(4,6-Dimethoxy-pyridin-3-yl)-9-ethoxy-8-methoxy-1,2,3,4,4a,10b-hexahydro-phenanthridin-2-ol meso-tartrate;

(2R,4aR,10bR)-6-(2-Dimethylamino-pyrimidin-5-yl)-9-ethoxy-8-methoxy-1,2,3,4,4a,10b-hexahydro-phenanthridin-2-ol meso-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one meso-tartrate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one meso-tartrate;
(2R,4aR,10bR)-6-(2,6-Dimethoxy-pyridin-3-yl)-9-ethoxy-8-methoxy-1,2,3,4,4a,10b-hexahydro-phenanthridin-2-ol D-malate;
(2R,4aR,10bR)-9-Ethoxy-8-methoxy-6-(6-pyrazol-1-yl-pyridin-3-yl)-1,2,3,4,4a,10b-hexahydro-phenanthridin-2-ol D-malate;
(2R,4aR,10bR)-9-Ethoxy-8-methoxy-6-(2-methoxy-pyrimidin-5-yl)-1,2,3,4,4a,10b-hexahydro-phenanthridin-2-ol D-malate;
(2R,4aR,10bR)-6-(2,4-Dimethoxy-pyrimidin-5-yl)-9-ethoxy-8-methoxy-1,2,3,4,4a,10b-hexahydro-phenanthridin-2-ol D-malate;
(2R,4aR,10bR)-6-(3,6-Dimethoxy-pyridazin-4-yl)-9-ethoxy-8-methoxy-1,2,3,4,4a,10b-hexahydro-phenanthridin-2-ol D-malate;
(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-malate;
(2R,4aR,10bR)-6-(4,6-Dimethoxy-pyridin-3-yl)-9-ethoxy-8-methoxy-1,2,3,4,4a,10b-hexahydro-phenanthridin-2-ol D-malate;
5-((2R,4aR,10bR)-9-Ethoxy-2-hydroxy-8-methoxy-1,2,3,4,4a,10b-hexahydro-phenanthridin-6-yl)-1-methyl-1H-pyridin-2-one D-malate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one D-malate;
(2R,4aR,10bR)-6-(2,6-Dimethoxy-pyridin-3-yl)-9-ethoxy-8-methoxy-1,2,3,4,4a,10b-hexahydro-phenanthridin-2-ol L-malate;
(2R,4aR,10bR)-9-Ethoxy-8-methoxy-6-pyrimidin-5-yl-1,2,3,4,4a,10b-hexahydro-phenanthridin-2-ol L-malate;
(2R,4aR,10bR)-9-Ethoxy-8-methoxy-6-(2-methoxy-pyrimidin-5-yl)-1,2,3,4,4a,10b-hexahydro-phenanthridin-2-ol L-malate;
(2R,4aR,10bR)-6-(2,4-Dimethoxy-pyrimidin-5-yl)-9-ethoxy-8-methoxy-1,2,3,4,4a,10b-hexahydro-phenanthridin-2-ol L-malate;
(2R,4aR,10bR)-9-Ethoxy-6-(6-imidazol-1-yl-pyridin-3-yl)-8-methoxy-1,2,3,4,4a,10b-hexahydro-phenanthridin-2-ol L-malate;
(2R,4aR,10bR)-6-(3,6-Dimethoxy-pyridazin-4-yl)-9-ethoxy-8-methoxy-1,2,3,4,4a,10b-hexahydro-phenanthridin-2-ol L-malate;
(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol L-malate;
(2R,4aR,10bR)-6-(4,6-Dimethoxy-pyridin-3-yl)-9-ethoxy-8-methoxy-1,2,3,4,4a,10b-hexahydro-phenanthridin-2-ol L-malate;
5-((2R,4aR,10bR)-9-Ethoxy-2-hydroxy-8-methoxy-1,2,3,4,4a,10b-hexahydro-phenanthridin-6-yl)-1-methyl-1H-pyridin-2-one L-malate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one L-malate;
(2R,4aR,10bR)-6-(2,6-Dimethoxy-pyridin-3-yl)-9-ethoxy-8-methoxy-1,2,3,4,4a,10b-hexahydro-phenanthridin-2-ol fumarate;
(2R,4aR,10bR)-9-Ethoxy-8-methoxy-6-pyrimidin-5-yl-1,2,3,4,4a,10b-hexahydro-phenanthridin-2-ol fumarate;
(2R,4aR,10bR)-9-Ethoxy-8-methoxy-6-(6-pyrazol-1-yl-pyridin-3-yl)-1,2,3,4,4a,10b-hexahydro-phenanthridin-2-ol fumarate;
(2R,4aR,10bR)-9-Ethoxy-8-methoxy-6-(2-methoxy-pyrimidin-5-yl)-1,2,3,4,4a,10b-hexahydro-phenanthridin-2-ol fumarate;
(2R,4aR,10bR)-6-(2,4-Dimethoxy-pyrimidin-5-yl)-9-ethoxy-8-methoxy-1,2,3,4,4a,10b-hexahydro-phenanthridin-2-ol fumarate;
(2R,4aR,10bR)-9-Ethoxy-6-(6-imidazol-1-yl-pyridin-3-yl)-8-methoxy-1,2,3,4,4a,10b-hexahydro-phenanthridin-2-ol fumarate;
(2R,4aR,10bR)-6-(3,6-Dimethoxy-pyridazin-4-yl)-9-ethoxy-8-methoxy-1,2,3,4,4a,10b-hexahydro-phenanthridin-2-ol fumarate;
(2R,4aR,10bR)-9-Ethoxy-8-methoxy-6-(6-methoxy-pyridin-3-yl)-1,2,3,4,4a,10b-hexahydro-phenanthridin-2-ol fumarate;
(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol fumarate;
(2R,4aR,10bR)-6-(4,6-Dimethoxy-pyridin-3-yl)-9-ethoxy-8-methoxy-1,2,3,4,4a,10b-hexahydro-phenanthridin-2-ol fumarate;
(2R,4aR,10bR)-6-(2-Dimethylamino-pyrimidin-5-yl)-9-ethoxy-8-methoxy-1,2,3,4,4a,10b-hexahydro-phenanthridin-2-ol fumarate;
5-((2R,4aR,10bR)-9-Ethoxy-2-hydroxy-8-methoxy-1,2,3,4,4a,10b-hexahydro-phenanthridin-6-yl)-1-methyl-1H-pyridin-2-one fumarate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one fumarate;
(2R,4aR,10bR)-6-(2,6-Dimethoxy-pyridin-3-yl)-9-ethoxy-8-methoxy-1,2,3,4,4a,10b-hexahydro-phenanthridin-2-ol maleinate;
(2R,4aR,10bR)-9-Ethoxy-8-methoxy-6-pyrimidin-5-yl-1,2,3,4,4a,10b-hexahydro-phenanthridin-2-ol maleinate;
(2R,4aR,10bR)-9-Ethoxy-8-methoxy-6-(2-methoxy-pyrimidin-5-yl)-1,2,3,4,4a,10b-hexahydro-phenanthridin-2-ol maleinate;
(2R,4aR,10bR)-6-(2,4-Dimethoxy-pyrimidin-5-yl)-9-ethoxy-8-methoxy-1,2,3,4,4a,10b-hexahydro-phenanthridin-2-ol maleinate;
(2R,4aR,10bR)-9-Ethoxy-8-methoxy-6-pyrazin-2-yl-1,2,3,4,4a,10b-hexahydro-phenanthridin-2-ol maleinate;
(2R,4aR,10bR)-6-(3,6-Dimethoxy-pyridazin-4-yl)-9-ethoxy-8-methoxy-1,2,3,4,4a,10b-hexahydro-phenanthridin-2-ol maleinate;
(2R,4aR,10bR)-9-Ethoxy-8-methoxy-6-(6-methoxy-pyridin-3-yl)-1,2,3,4,4a,10b-hexahydro-phenanthridin-2-ol maleinate;
(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol maleinate;
(2R,4aR,10bR)-6-(4,6-Dimethoxy-pyridin-3-yl)-9-ethoxy-8-methoxy-1,2,3,4,4a,10b-hexahydro-phenanthridin-2-ol maleinate;
(2R,4aR,10bR)-6-(2-Dimethylamino-pyrimidin-5-yl)-9-ethoxy-8-methoxy-1,2,3,4,4a,10b-hexahydro-phenanthridin-2-ol maleinate;
5-((2R,4aR,10bR)-9-Ethoxy-2-hydroxy-8-methoxy-1,2,3,4,4a,10b-hexahydro-phenanthridin-6-yl)-1-methyl-1H-pyridin-2-one maleinate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one maleinate;

(2R,4aR,10bR)-6-(2,6-Dimethoxy-pyridin-3-yl)-9-ethoxy-8-methoxy-1,2,3,4,4a,10b-hexahydro-phenanthridin-2-ol 2-oxoglutarate;

(2R,4aR,10bR)-9-Ethoxy-8-methoxy-6-pyrimidin-5-yl-1,2,3,4,4a,10b-hexahydro-phenanthridin-2-ol 2-oxoglutarate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol 2-oxoglutarate;

(2R,4aR,10bR)-9-Ethoxy-8-methoxy-6-(2-methoxy-pyrimidin-5-yl)-1,2,3,4,4a,10b-hexahydro-phenanthridin-2-ol 2-oxoglutarate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol 2-oxoglutarate;

(2R,4aR,10bR)-9-Ethoxy-8-methoxy-6-pyrazin-2-yl-1,2,3,4,4a,10b-hexahydro-phenanthridin-2-ol 2-oxoglutarate;

(2R,4aR,10bR)-6-(3,6-Dimethoxy-pyridazin-4-yl)-9-ethoxy-8-methoxy-1,2,3,4,4a,10b-hexahydro-phenanthridin-2-ol 2-oxoglutarate;

(2R,4aR,10bR)-9-Ethoxy-8-methoxy-6-(6-methoxy-pyridin-3-yl)-1,2,3,4,4a,10b-hexahydro-phenanthridin-2-ol 2-oxoglutarate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol 2-oxoglutarate;

(2R,4aR,10bR)-6-(4,6-Dimethoxy-pyridin-3-yl)-9-ethoxy-8-methoxy-1,2,3,4,4a,10b-hexahydro-phenanthridin-2-ol 2-oxoglutarate;

(2R,4aR,10bR)-6-(2-Dimethylamino-pyrimidin-5-yl)-9-ethoxy-8-methoxy-1,2,3,4,4a,10b-hexahydro-phenanthridin-2-ol 2-oxoglutarate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one 2-oxoglutarate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one 2-oxoglutarate;

(2R,4aR,10bR)-6-(2,6-Dimethoxy-pyridin-3-yl)-9-ethoxy-8-methoxy-1,2,3,4,4a,10b-hexahydro-phenanthridin-2-ol oxalate;

(2R,4aR,10bR)-9-Ethoxy-8-methoxy-6-pyrimidin-5-yl-1,2,3,4,4a,10b-hexahydro-phenanthridin-2-ol oxalate;

(2R,4aR,10bR)-9-Ethoxy-8-methoxy-6-(2-methoxy-pyrimidin-5-yl)-1,2,3,4,4a,10b-hexahydro-phenanthridin-2-ol oxalate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol oxalate;

(2R,4aR,10bR)-9-Ethoxy-6-(6-imidazol-1-yl-pyridin-3-yl)-8-methoxy-1,2,3,4,4a,10b-hexahydro-phenanthridin-2-ol oxalate;

(2R,4aR,10bR)-6-(3,6-Dimethoxy-pyridazin-4-yl)-9-ethoxy-8-methoxy-1,2,3,4,4a,10b-hexahydro-phenanthridin-2-ol oxalate;

(2R,4aR,10bR)-6-(4,6-Dimethoxy-pyridin-3-yl)-9-ethoxy-8-methoxy-1,2,3,4,4a,10b-hexahydro-phenanthridin-2-ol oxalate;

(2R,4aR,10bR)-6-(2-Dimethylamino-pyrimidin-5-yl)-9-ethoxy-8-methoxy-1,2,3,4,4a,10b-hexahydro-phenanthridin-2-ol oxalate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one oxalate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one oxalate;

(2R,4aR,10bR)-6-(2,6-Dimethoxy-pyridin-3-yl)-9-ethoxy-8-methoxy-1,2,3,4,4a,10b-hexahydro-phenanthridin-2-ol D-gluconate;

(2R,4aR,10bR)-9-Ethoxy-8-methoxy-6-pyrimidin-5-yl-1,2,3,4,4a,10b-hexahydro-phenanthridin-2-ol D-gluconate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol D-gluconate;

(2R,4aR,10bR)-9-Ethoxy-8-methoxy-6-(2-methoxy-pyrimidin-5-yl)-1,2,3,4,4a,10b-hexahydro-phenanthridin-2-ol D-gluconate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol D-gluconate;

(2R,4aR,10bR)-9-Ethoxy-8-methoxy-6-pyrazin-2-yl-1,2,3,4,4a,10b-hexahydro-phenanthridin-2-ol D-gluconate;

(2R,4aR,10bR)-6-(3,6-Dimethoxy-pyridazin-4-yl)-9-ethoxy-8-methoxy-1,2,3,4,4a,10b-hexahydro-phenanthridin-2-ol D-gluconate;

(2R,4aR,10bR)-9-Ethoxy-8-methoxy-6-(6-methoxy-pyridin-3-yl)-1,2,3,4,4a,10b-hexahydro-phenanthridin-2-ol D-gluconate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-gluconate;

(2R,4aR,10bR)-6-(4,6-Dimethoxy-pyridin-3-yl)-9-ethoxy-8-methoxy-1,2,3,4,4a,10b-hexahydro-phenanthridin-2-ol D-gluconate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one D-gluconate; and 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one D-gluconate.

2. A salt according to claim 1 which is selected from the group consisting of (2R,4aR,10bR)-6-(2,6-Dimethoxy-pyridin-3-yl)-9-ethoxy-8-methoxy-1,2,3,4,4a,10b-hexahydro-phenanthridin-2-ol hydrochloride;

(2R,4aR,10bR)-9-Ethoxy-8-methoxy-6-pyrimidin-5-yl-1,2,3,4,4a,10b-hexahydro-phenanthridin-2-ol hydrochloride;

(2R,4aR,10bR)-9-Ethoxy-8-methoxy-6-(6-pyrazol-1-yl-pyridin-3-yl)-1,2,3,4,4a,10b-hexahydro-phenanthridin-2-ol hydrochloride;

(2R,4aR,10bR)-9-Ethoxy-8-methoxy-6-(2-methoxy-pyrimidin-5-yl)-1,2,3,4,4a,10b-hexahydro-phenanthridin-2-ol hydrochloride;

(2R,4aR,10bR)-6-(2,4-Dimethoxy-pyrimidin-5-yl)-9-ethoxy-8-methoxy-1,2,3,4,4a,10b-hexahydro-phenanthridin-2-ol hydrochloride;

(2R,4aR,10bR)-9-Ethoxy-8-methoxy-6-pyrazin-2-yl-1,2,3,4,4a,10b-hexahydro-phenanthridin-2-ol hydrochloride;

(2R,4aR,10bR)-6-(3,6-Dimethoxy-pyridazin-4-yl)-9-ethoxy-8-methoxy-1,2,3,4,4a,10b-hexahydro-phenanthridin-2-ol hydrochloride;

(2R,4aR,10bR)-9-Ethoxy-8-methoxy-6-(6-methoxy-pyridin-3-yl)-1,2,3,4,4a,10b-hexahydro-phenanthridin-2-ol hydrochloride;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol hydrochloride;

(2R,4aR,10bR)-6-(4,6-Dimethoxy-pyridin-3-yl)-9-ethoxy-8-methoxy-1,2,3,4,4a,10b-hexahydro-phenanthridin-2-ol hydrochloride;

(2R,4aR,10bR)-6-(2-Dimethylamino-pyrimidin-5-yl)-9-ethoxy-8-methoxy-1,2,3,4,4a,10b-hexahydro-phenanthridin-2-ol hydrochloride;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one hydrochloride;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one hydrochloride;

(2R,4aR,10bR)-6-(2,6-Dimethoxy-pyridin-3-yl)-9-ethoxy-8-methoxy-1,2,3,4,4a,10b-hexahydro-phenanthridin-2-ol sulfate;

(2R,4aR,10bR)-9-Ethoxy-8-methoxy-6-(2-methoxy-pyrimidin-5-yl)-1,2,3,4,4a,10b-hexahydro-phenanthridin-2-ol sulfate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol sulfate;

(2R,4aR,10bR)-9-Ethoxy-6-(6-imidazol-1-yl-pyridin-3-yl)-8-methoxy-1,2,3,4,4a,10b-hexahydro-phenanthridin-2-ol sulfate;

(2R,4aR,10bR)-6-(3,6-Dimethoxy-pyridazin-4-yl)-9-ethoxy-8-methoxy-1,2,3,4,4a,10b-hexahydro-phenanthridin-2-ol sulfate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol sulfate;

(2R,4aR,10bR)-6-(4,6-Dimethoxy-pyridin-3-yl)-9-ethoxy-8-methoxy-1,2,3,4,4a,10b-hexahydro-phenanthridin-2-ol sulfate;

(2R,4aR,10bR)-6-(2-Dimethylamino-pyrimidin-5-yl)-9-ethoxy-8-methoxy-1,2,3,4,4a,10b-hexahydro-phenanthridin-2-ol sulfate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one sulfate;

(2R,4aR,10bR)-6-(2,6-Dimethoxy-pyridin-3-yl)-9-ethoxy-8-methoxy-1,2,3,4,4a,10b-hexahydro-phenanthridin-2-ol methansulfonate;

(2R,4aR,10bR)-9-Ethoxy-8-methoxy-6-pyrimidin-5-yl-1,2,3,4,4a,10b-hexahydro-phenanthridin-2-ol methansulfonate;

(2R,4aR,10bR)-9-Ethoxy-8-methoxy-6-(2-methoxy-pyrimidin-5-yl)-1,2,3,4,4a,10b-hexahydro-phenanthridin-2-ol methansulfonate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol methansulfonate;

(2R,4aR,10bR)-9-Ethoxy-6-(6-imidazol-1-yl-pyridin-3-yl)-8-methoxy-1,2,3,4,4a,10b-hexahydro-phenanthridin-2-ol methansulfonate;

(2R,4aR,10bR)-9-Ethoxy-8-methoxy-6-pyrazin-2-yl-1,2,3,4,4a,10b-hexahydro-phenanthridin-2-ol methansulfonate;

(2R,4aR,10bR)-6-(3,6-Dimethoxy-pyridazin-4-yl)-9-ethoxy-8-methoxy-1,2,3,4,4a,10b-hexahydro-phenanthridin-2-ol methansulfonate;

(2R,4aR,10bR)-9-Ethoxy-8-methoxy-6-(6-methoxy-pyridin-3-yl)-1,2,3,4,4a,10b-hexahydro-phenanthridin-2-ol methansulfonate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol methansulfonate;

(2R,4aR,10bR)-6-(4,6-Dimethoxy-pyridin-3-yl)-9-ethoxy-8-methoxy-1,2,3,4,4a,10b-hexahydro-phenanthridin-2-ol methansulfonate;

(2R,4aR,10bR)-6-(2-Dimethylamino-pyrimidin-5-yl)-9-ethoxy-8-methoxy-1,2,3,4,4a,10b-hexahydro-phenanthridin-2-ol methansulfonate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one methansulfonate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one methansulfonate;

(2R,4aR,10bR)-6-(2,6-Dimethoxy-pyridin-3-yl)-9-ethoxy-8-methoxy-1,2,3,4,4a,10b-hexahydro-phenanthridin-2-ol citrate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol citrate;

(2R,4aR,10bR)-9-Ethoxy-8-methoxy-6-(2-methoxy-pyrimidin-5-yl)-1,2,3,4,4a,10b-hexahydro-phenanthridin-2-ol citrate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol citrate;

(2R,4aR,10bR)-9-Ethoxy-6-(6-imidazol-1-yl-pyridin-3-yl)-8-methoxy-1,2,3,4,4a,10b-hexahydro-phenanthridin-2-ol citrate;

(2R,4aR,10bR)-6-(3,6-Dimethoxy-pyridazin-4-yl)-9-ethoxy-8-methoxy-1,2,3,4,4a,10b-hexahydro-phenanthridin-2-ol citrate;

(2R,4aR,10bR)-9-Ethoxy-8-methoxy-6-(6-methoxy-pyridin-3-yl)-1,2,3,4,4a,10b-hexahydro-phenanthridin-2-ol citrate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol citrate;

(2R,4aR,10bR)-6-(4,6-Dimethoxy-pyridin-3-yl)-9-ethoxy-8-methoxy-1,2,3,4,4a,10b-hexahydro-phenanthridin-2-ol citrate;

(2R,4aR,10bR)-6-(2-Dimethylamino-pyrimidin-5-yl)-9-ethoxy-8-methoxy-1,2,3,4,4a,10b-hexahydro-phenanthridin-2-ol citrate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one citrate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one citrate;

(2R,4aR,10bR)-6-(2,6-Dimethoxy-pyridin-3-yl)-9-ethoxy-8-methoxy-1,2,3,4,4a,10b-hexahydro-phenanthridin-2-ol L-tartrate;

(2R,4aR,10bR)-9-Ethoxy-8-methoxy-6-pyrimidin-5-yl-1,2,3,4,4a,10b-hexahydro-phenanthridin-2-ol L-tartrate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol L-tartrate;

(2R,4aR,10bR)-9-Ethoxy-8-methoxy-6-(2-methoxy-pyrimidin-5-yl)-1,2,3,4,4a,10b-hexahydro-phenanthridin-2-ol L-tartrate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol L-tartrate;

(2R,4aR,10bR)-9-Ethoxy-8-methoxy-6-pyrazin-2-yl-1,2,3,4,4a,10b-hexahydro-phenanthridin-2-ol L-tartrate;

(2R,4aR,10bR)-6-(3,6-Dimethoxy-pyridazin-4-yl)-9-ethoxy-8-methoxy-1,2,3,4,4a,10b-hexahydro-phenanthridin-2-ol L-tartrate;

(2R,4aR,10bR)-9-Ethoxy-8-methoxy-6-(6-methoxy-pyridin-3-yl)-1,2,3,4,4a,10b-hexahydro-phenanthridin-2-ol L-tartrate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol L-tartrate;

(2R,4aR,10bR)-6-(4,6-Dimethoxy-pyridin-3-yl)-9-ethoxy-8-methoxy-1,2,3,4,4a,10b-hexahydro-phenanthridin-2-ol L-tartrate;

(2R,4aR,10bR)-6-(2-Dimethylamino-pyrimidin-5-yl)-9-ethoxy-8-methoxy-1,2,3,4,4a,10b-hexahydro-phenanthridin-2-ol L-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one L-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one L-tartrate;

(2R,4aR,10bR)-6-(2,6-Dimethoxy-pyridin-3-yl)-9-ethoxy-8-methoxy-1,2,3,4,4a,10b-hexahydro-phenanthridin-2-ol D-tartrate;

(2R,4aR,10bR)-9-Ethoxy-8-methoxy-6-(2-methoxy-pyrimidin-5-yl)-1,2,3,4,4a,10b-hexahydro-phenanthridin-2-ol D-tartrate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol D-tartrate;

(2R,4aR,10bR)-9-Ethoxy-6-(6-imidazol-1-yl-pyridin-3-yl)-8-methoxy-1,2,3,4,4a,10b-hexahydro-phenanthridin-2-ol D-tartrate;

(2R,4aR,10bR)-9-Ethoxy-8-methoxy-6-pyrazin-2-yl-1,2,3,4,4a,10b-hexahydro-phenanthridin-2-ol D-tartrate;

(2R,4aR,10bR)-6-(3,6-Dimethoxy-pyridazin-4-yl)-9-ethoxy-8-methoxy-1,2,3,4,4a,10b-hexahydro-phenanthridin-2-ol D-tartrate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-tartrate;

(2R,4aR,10bR)-6-(4,6-Dimethoxy-pyridin-3-yl)-9-ethoxy-8-methoxy-1,2,3,4,4a,10b-hexahydro-phenanthridin-2-ol D-tartrate;

(2R,4aR,10bR)-6-(2-Dimethylamino-pyrimidin-5-yl)-9-ethoxy-8-methoxy-1,2,3,4,4a,10b-hexahydro-phenanthridin-2-ol D-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one D-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one D-tartrate;

(2R,4aR,10bR)-6-(2,6-Dimethoxy-pyridin-3-yl)-9-ethoxy-8-methoxy-1,2,3,4,4a,10b-hexahydro-phenanthridin-2-ol meso-tartrate;

(2R,4aR,10bR)-9-Ethoxy-8-methoxy-6-pyrimidin-5-yl-1,2,3,4,4a,10b-hexahydro-phenanthridin-2-ol meso-tartrate;

(2R,4aR,10bR)-9-Ethoxy-8-methoxy-6-(2-methoxy-pyrimidin-5-yl)-1,2,3,4,4a,10b-hexahydro-phenanthridin-2-ol meso-tartrate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol meso-tartrate;

(2R,4aR,10bR)-9-Ethoxy-6-(6-imidazol-1-yl-pyridin-3-yl)-8-methoxy-1,2,3,4,4a,10b-hexahydro-phenanthridin-2-ol meso-tartrate;

(2R,4aR,10bR)-9-Ethoxy-8-methoxy-6-pyrazin-2-yl-1,2,3,4,4a,10b-hexahydro-phenanthridin-2-ol meso-tartrate;

(2R,4aR,10bR)-6-(3,6-Dimethoxy-pyridazin-4-yl)-9-ethoxy-8-methoxy-1,2,3,4,4a,10b-hexahydro-phenanthridin-2-ol meso-tartrate;

(2R,4aR,10b R)-6-(2-Dimethylamino-4-methoxy-pyrimidin-5-yl)-9-ethoxy-8-methoxy-1,2,3,4,4a,10b-hexahydro-phenanthridin-2-ol meso-tartrate;

(2R,4aR,10bR)-6-(4,6-Dimethoxy-pyridin-3-yl)-9-ethoxy-8-methoxy-1,2,3,4,4a,10b-hexahydro-phenanthridin-2-ol meso-tartrate;

(2R,4aR,10bR)-6-(2-Dimethylamino-pyrimidin-5-yl)-9-ethoxy-8-methoxy-1,2,3,4,4a,10b-hexahydro-phenanthridin-2-ol meso-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one meso-tartrate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one meso-tartrate;

(2R,4aR,10bR)-6-(2,6-Dimethoxy-pyridin-3-yl)-9-ethoxy-8-methoxy-1,2,3,4,4a,10b-hexahydro-phenanthridin-2-ol D-malate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol D-malate;

(2R,4aR,10bR)-9-Ethoxy-8-methoxy-6-(2-methoxy-pyrimidin-5-yl)-1,2,3,4,4a,10b-hexahydro-phenanthridin-2-ol D-malate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol D-malate;

(2R,4aR,10bR)-6-(3,6-Dimethoxy-pyridazin-4-yl)-9-ethoxy-8-methoxy-1,2,3,4,4a,10b-hexahydro-phenanthridin-2-ol D-malate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-malate;

(2R,4aR,10bR)-6-(4,6-Dimethoxy-pyridin-3-yl)-9-ethoxy-8-methoxy-1,2,3,4,4a,10b-hexahydro-phenanthridin-2-ol D-malate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one D-malate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one D-malate;

(2R,4aR,10bR)-6-(2,6-Dimethoxy-pyridin-3-yl)-9-ethoxy-8-methoxy-1,2,3,4,4a,10b-hexahydro-phenanthridin-2-ol L-malate;

(2R,4aR,10bR)-9-Ethoxy-8-methoxy-6-pyrimidin-5-yl-1,2,3,4,4a,10b-hexahydro-phenanthridin-2-ol L-malate;

(2R,4aR,10bR)-9-Ethoxy-8-methoxy-6-(2-methoxy-pyrimidin-5-yl)-1,2,3,4,4a,10b-hexahydro-phenanthridin-2-ol L-malate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol L-malate;

(2R,4aR,10bR)-9-Ethoxy-6-(6-imidazol-1-yl-pyridin-3-yl)-8-methoxy-1,2,3,4,4a,10b-hexahydro-phenanthridin-2-ol L-malate;

(2R,4aR,10bR)-6-(3,6-Dimethoxy-pyridazin-4-yl)-9-ethoxy-8-methoxy-1,2,3,4,4a,10b-hexahydro-phenanthridin-2-ol L-malate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol L-malate;
(2R,4aR,10bR)-6-(4,6-Dimethoxy-pyridin-3-yl)-9-ethoxy-8-methoxy-1,2,3,4,4a,10b-hexahydro-phenanthridin-2-ol L-malate;
5-((2R,4aR,10bR)-9-Ethoxy-2-hydroxy-8-methoxy-1,2,3,4,4a,10b-hexahydro-phenanthridin-6-yl)-1-methyl-1H-pyridin-2-one L-malate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one L-malate;
(2R,4aR,10bR)-6-(2,6-Dimethoxy-pyridin-3-yl)-9-ethoxy-8-methoxy-1,2,3,4,4a,10b-hexahydro-phenanthridin-2-ol fumarate;
(2R,4aR,10bR)-9-Ethoxy-8-methoxy-6-pyrimidin-5-yl-1,2,3,4,4a,10b-hexahydro-phenanthridin-2-ol fumarate;
(2R,4aR,10bR)-9-Ethoxy-8-methoxy-6-(6-pyrazol-1-yl-pyridin-3-yl)-1,2,3,4,4a,10b-hexahydro-phenanthridin-2-ol fumarate;
(2R,4aR,10bR)-9-Ethoxy-8-methoxy-6-(2-methoxy-pyrimidin-5-yl)-1,2,3,4,4a,10b-hexahydro-phenanthridin-2-ol fumarate;
(2R,4aR,10bR)-6-(2,4-Dimethoxy-pyrimidin-5-yl)-9-ethoxy-8-methoxy-1,2,3,4,4a,10b-hexahydro-phenanthridin-2-ol fumarate;
(2R,4aR,10bR)-9-Ethoxy-6-(6-imidazol-1-yl-pyridin-3-yl)-8-methoxy-1,2,3,4,4a,10b-hexahydro-phenanthridin-2-ol fumarate;
(2R,4aR,10bR)-6-(3,6-Dimethoxy-pyridazin-4-yl)-9-ethoxy-8-methoxy-1,2,3,4,4a,10b-hexahydro-phenanthridin-2-ol fumarate;
(2R,4aR,10bR)-9-Ethoxy-8-methoxy-6-(6-methoxy-pyridin-3-yl)-1,2,3,4,4a,10b-hexahydro-phenanthridin-2-ol fumarate;
(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol fumarate;
(2R,4aR,10bR)-6-(4,6-Dimethoxy-pyridin-3-yl)-9-ethoxy-8-methoxy-1,2,3,4,4a,10b-hexahydro-phenanthridin-2-ol fumarate;
(2R,4aR,10bR)-6-(2-Dimethylamino-pyrimidin-5-yl)-9-ethoxy-8-methoxy-1,2,3,4,4a,10b-hexahydro-phenanthridin-2-ol fumarate;
5-((2R,4aR,10bR)-9-Ethoxy-2-hydroxy-8-methoxy-1,2,3,4,4a,10b-hexahydro-phenanthridin-6-yl)-1-methyl-1H-pyridin-2-one fumarate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one fumarate;
(2R,4aR,10bR)-6-(2,6-Dimethoxy-pyridin-3-yl)-9-ethoxy-8-methoxy-1,2,3,4,4a,10b-hexahydro-phenanthridin-2-ol maleinate;
(2R,4aR,10bR)-9-Ethoxy-8-methoxy-6-pyrimidin-5-yl-1,2,3,4,4a,10b-hexahydro-phenanthridin-2-ol maleinate;
(2R,4aR,10bR)-9-Ethoxy-8-methoxy-6-(2-methoxy-pyrimidin-5-yl)-1,2,3,4,4a,10b-hexahydro-phenanthridin-2-ol maleinate;
(2R,4aR,10bR)-6-(2,4-Dimethoxy-pyrimidin-5-yl)-9-ethoxy-8-methoxy-1,2,3,4,4a,10b-hexahydro-phenanthridin-2-ol maleinate;
(2R,4aR,10bR)-9-Ethoxy-8-methoxy-6-pyrazin-2-yl-1,2,3,4,4a,10b-hexahydro-phenanthridin-2-ol maleinate;
(2R,4aR,10bR)-6-(3,6-Dimethoxy-pyridazin-4-yl)-9-ethoxy-8-methoxy-1,2,3,4,4a,10b-hexahydro-phenanthridin-2-ol maleinate;
(2R,4aR,10bR)-9-Ethoxy-8-methoxy-6-(6-methoxy-pyridin-3-yl)-1,2,3,4,4a,10b-hexahydro-phenanthridin-2-ol maleinate;
(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol maleinate;
(2R,4aR,10bR)-6-(4,6-Dimethoxy-pyridin-3-yl)-9-ethoxy-8-methoxy-1,2,3,4,4a,10b-hexahydro-phenanthridin-2-ol maleinate;
(2R,4aR,10bR)-6-(2-Dimethylamino-pyrimidin-5-yl)-9-ethoxy-8-methoxy-1,2,3,4,4a,10b-hexahydro-phenanthridin-2-ol maleinate;
5-((2R,4aR,10bR)-9-Ethoxy-2-hydroxy-8-methoxy-1,2,3,4,4a,10b-hexahydro-phenanthridin-6-yl)-1-methyl-1H-pyridin-2-one maleinate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one maleinate;
(2R,4aR,10bR)-6-(2,6-Dimethoxy-pyridin-3-yl)-9-ethoxy-8-methoxy-1,2,3,4,4a,10b-hexahydro-phenanthridin-2-ol 2-oxoglutarate;
(2R,4aR,10bR)-9-Ethoxy-8-methoxy-6-pyrimidin-5-yl-1,2,3,4,4a,10b-hexahydro-phenanthridin-2-ol 2-oxoglutarate;
(2R,4aR,10bR)-9-Ethoxy-8-methoxy-6-(6-pyrazol-1-yl-pyridin-3-yl)-1,2,3,4,4a,10b-hexahydro-phenanthridin-2-ol 2-oxoglutarate;
(2R,4aR,10bR)-9-Ethoxy-8-methoxy-6-(2-methoxy-pyrimidin-5-yl)-1,2,3,4,4a,10b-hexahydro-phenanthridin-2-ol 2-oxoglutarate;
(2R,4aR,10bR)-6-(2,4-Dimethoxy-pyrimidin-5-yl)-9-ethoxy-8-methoxy-1,2,3,4,4a,10b-hexahydro-phenanthridin-2-ol 2-oxoglutarate;
(2R,4aR,10bR)-9-Ethoxy-6-(6-imidazol-1-yl-pyridin-3-yl)-8-methoxy-1,2,3,4,4a,10b-hexahydro-phenanthridin-2-ol 2-oxoglutarate;
(2R,4aR,10bR)-9-Ethoxy-8-methoxy-6-pyrazin-2-yl-1,2,3,4,4a,10b-hexahydro-phenanthridin-2-ol 2-oxoglutarate;
(2R,4aR,10bR)-6-(3,6-Dimethoxy-pyridazin-4-yl)-9-ethoxy-8-methoxy-1,2,3,4,4a,10b-hexahydro-phenanthridin-2-ol 2-oxoglutarate;
(2R,4aR,10bR)-9-Ethoxy-8-methoxy-6-(6-methoxy-pyridin-3-yl)-1,2,3,4,4a,10b-hexahydro-phenanthridin-2-ol 2-oxoglutarate;
(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol 2-oxoglutarate;
(2R,4aR,10bR)-6-(4,6-Dimethoxy-pyridin-3-yl)-9-ethoxy-8-methoxy-1,2,3,4,4a,10b-hexahydro-phenanthridin-2-ol 2-oxoglutarate;
(2R,4aR,10bR)-6-(2-Dimethylamino-pyrimidin-5-yl)-9-ethoxy-8-methoxy-1,2,3,4,4a,10b-hexahydro-phenanthridin-2-ol 2-oxoglutarate;
5-((2R,4aR,10bR)-9-Ethoxy-2-hydroxy-8-methoxy-1,2,3,4,4a,10b-hexahydro-phenanthridin-6-yl)-1-methyl-1H-pyridin-2-one 2-oxoglutarate;
5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one 2-oxoglutarate;
(2R,4aR,10bR)-6-(2,6-Dimethoxy-pyridin-3-yl)-9-ethoxy-8-methoxy-1,2,3,4,4a,10b-hexahydro-phenanthridin-2-ol oxalate;
(2R,4aR,10bR)-9-Ethoxy-8-methoxy-6-pyrimidin-5-yl-1,2,3,4,4a,10b-hexahydro-phenanthridin-2-ol oxalate;

(2R,4aR,10bR)-9-Ethoxy-8-methoxy-6-(2-methoxy-pyrimidin-5-yl)-1,2,3,4,4a,10b-hexahydro-phenanthridin-2-ol oxalate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol oxalate;

(2R,4aR,10bR)-9-Ethoxy-6-(6-imidazol-1-yl-pyridin-3-yl)-8-methoxy-1,2,3,4,4a,10b-hexahydro-phenanthridin-2-ol oxalate;

(2R,4aR,10bR)-6-(3,6-Dimethoxy-pyridazin-4-yl)-9-ethoxy-8-methoxy-1,2,3,4,4a,10b-hexahydro-phenanthridin-2-ol oxalate;

(2R,4aR,10bR)-6-(4,6-Dimethoxy-pyridin-3-yl)-9-ethoxy-8-methoxy-1,2,3,4,4a,10b-hexahydro-phenanthridin-2-ol oxalate;

(2R,4aR,10bR)-6-(2-Dimethylamino-pyrimidin-5-yl)-9-ethoxy-8-methoxy-1,2,3,4,4a,10b-hexahydro-phenanthridin-2-ol oxalate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one oxalate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one oxalate;

(2R,4aR,10bR)-6-(2,6-Dimethoxy-pyridin-3-yl)-9-ethoxy-8-methoxy-1,2,3,4,4a,10b-hexahydro-phenanthridin-2-ol D-gluconate;

(2R,4aR,10bR)-9-Ethoxy-8-methoxy-6-pyrimidin-5-yl-1,2,3,4,4a,10b-hexahydro-phenanthridin-2-ol D-gluconate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol D-gluconate;

(2R,4aR,10bR)-9-Ethoxy-8-methoxy-6-(2-methoxy-pyrimidin-5-yl)-1,2,3,4,4a,10b-hexahydro-phenanthridin-2-ol D-gluconate;

(2R,4aR,10bR)-6-(2,4-Dimethoxy-pyrimidin-5-yl)-9-ethoxy-8-methoxy-1,2,3,4,4a,10b-hexahydro-phenanthridin-2-ol D-gluconate;

(2R,4aR,10bR)-9-Ethoxy-8-methoxy-6-pyrazin-2-yl-1,2,3,4,4a,10b-hexahydro-phenanthridin-2-ol D-gluconate;

(2R,4aR,10bR)-6-(3,6-Dimethoxy-pyridazin-4-yl)-9-ethoxy-8-methoxy-1,2,3,4,4a,10b-hexahydro-phenanthridin-2-ol D-gluconate;

(2R,4aR,10bR)-9-Ethoxy-8-methoxy-6-(6-methoxy-pyridin-3-yl)-1,2,3,4,4a,10b-hexahydro-phenanthridin-2-ol D-gluconate;

(2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-gluconate;

(2R, 4aR,10bR)-6-(4,6-Dimethoxy-pyridin-3-yl)-9-ethoxy-8-methoxy-1,2,3,4,4a,10b-hexahydro-phenanthridin-2-ol D-gluconate;

5-((2R,4aR,10bR)-9-Ethoxy-2-hydroxy-8-methoxy-1,2,3,4,4a,10b-hexahydro-phenanthridin-6-yl)-1-methyl-1H-pyridin-2-one D-gluconate;

5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one D-gluconate;

(2R,4aR,10bR)-9-Ethoxy-8-methoxy-6-(6-pyrazol-1-yl-pyridin-3-yl)-1,2,3,4,4a,10b-hexahydro-phenanthridin-2-ol oxalate; and (2R,4aR,10bR)-9-Ethoxy-8-methoxy-6-pyrazin-2-yl-1,2,3,4,4a,10b-hexahydro-phenanthridin-2-ol oxalate.

3. A pharmaceutical composition comprising one or more salts as claimed in claim 1 together with a pharmaceutical auxiliary and/or excipient.

4. A pharmaceutical composition according to claim 3, which in a solid dosage form.

5. A method for treating asthma in a patient comprising administering to said patient a therapeutically effective amount of a salt as claimed in claim 1.

* * * * *

UNITED STATES PATENT AND TRADEMARK OFFICE
CERTIFICATE OF CORRECTION

PATENT NO.       : 7,718,668 B2                                  Page 1 of 1
APPLICATION NO.  : 11/884934
DATED            : May 18, 2010
INVENTOR(S)      : Ulrich Kautz et al.

It is certified that error appears in the above-identified patent and that said Letters Patent is hereby corrected as shown below:

Column 49, Claim 1, After Line 15 and Before Line 16
Please insert the following formula:
-- (2R,4aR,10bR)-9-Ethoxy-6-(6-imidazol-1-yl-pyridin-3-yl)-8-methoxy-1,2,3,4,4a,10b-hexahydro-phenanthridin-2-ol 2-oxoglutarate; --

Column 58, Claim 4, Line 33
Please delete "in"
and replace with -- is --

Signed and Sealed this

Third Day of August, 2010

David J. Kappos
*Director of the United States Patent and Trademark Office*